(12) United States Patent
Tomikawa et al.

(10) Patent No.: US 8,614,080 B2
(45) Date of Patent: Dec. 24, 2013

(54) METHOD FOR PRODUCING HYDROXYLATED ADAMANTANE USING CYTOCHROME P450

(71) Applicant: Shionogi & Co., Ltd., Osaka (JP)

(72) Inventors: Taijiro Tomikawa, Osaka (JP); Yuuichi Mitsuda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/679,896

(22) Filed: Nov. 16, 2012

(65) Prior Publication Data

US 2013/0072668 A1    Mar. 21, 2013

Related U.S. Application Data

(62) Division of application No. 12/678,281, filed as application No. PCT/JP2008/067248 on Sep. 25, 2008, now Pat. No. 8,383,381.

(30) Foreign Application Priority Data

Sep. 27, 2007  (JP) ................................ 2007-250617

(51) Int. Cl.
   *C12N 9/04*    (2006.01)
(52) U.S. Cl.
   USPC ........................................................ 435/190
(58) Field of Classification Search
   None
   See application file for complete search history.

(56) References Cited

U.S. PATENT DOCUMENTS

| 7,049,111 B1 | 5/2006 | Endo et al. |
| 2006/0154348 A1 | 7/2006 | Endo et al. |
| 2008/0220419 A1 | 9/2008 | Kubota et al. |

FOREIGN PATENT DOCUMENTS

| EP | 1148122 A1 | 10/2001 |
| EP | 1 500 704 A1 | 1/2005 |
| EP | 1712542 A1 | 10/2006 |
| EP | 1 894 919 | 3/2008 |
| EP | 1 953 145 A1 | 8/2008 |
| EP | 2 006 286 A2 | 12/2008 |
| EP | 2 088 136 A1 | 8/2009 |
| JP | 06-070780 A | 3/1994 |
| JP | 2006-63061 | 3/2006 |
| JP | 2007132259 A | 5/2007 |
| WO | WO-00/44886 A1 | 8/2000 |
| WO | WO-03/087381 A1 | 10/2003 |
| WO | WO-2004-056744 A1 | 7/2004 |
| WO | WO-2006051729 A1 | 5/2006 |
| WO | WO-2006-132197 A1 | 12/2006 |
| WO | WO-2007/058346 A1 | 5/2007 |
| WO | WO-2007/114124 A1 | 10/2007 |
| WO | WO-2007/114125 A1 | 10/2007 |
| WO | WO-2008/053652 A1 | 5/2008 |
| WO | WO-2008142986 A1 | 11/2008 |

OTHER PUBLICATIONS

Johnson, R.A., et al., "Selective Oxygenation of Adamantanes and Other Substrates by *Beauveria sulfurescens*", J. Org. Chem., 1992, vol. 57, pp. 7209-7212.

Herr, M.E., et al., "The Microbiological Oxygenation of Acylated 1-Adamantanamines. Stereochemistry and Structural Determinations", The Journal of Organic Chemistry, 1968, vol. 33, pp. 3201-3207.

Watanabe, I., et al., "Cloning, characterization and expression of the gene encoding cytochrome *P*-450sca-2 from *Streptomyces carbophilus* involved in production of pravastatin, a specific HMG-CoA reductase inhibitor", Gene, 1995, vol. 163, pp. 81-85.

White, R.E. et al., "Regioselectivity in the cytochromes *P*-450: Control by protein Constraints and by Chemical Reactives", Archives of Biochemistry and Biophysics., 1984, vol. 228, pp. 493-502.

Mitsukura, K., et al., "Regioselective hydroxylation of adamantane by *Streptomyces griseoplanus* cells", Appl. Microbiol. Biotechnol., 2006, vol. 71, pp. 502-504.

Nodate, M., et al., "Functional expression system for cytochrome P450 genes using the reductase domain of self-sufficient P450RhF from *Rhodococcus* sp. NCIMB 9784", Appl. Microbiol. Biotechnol., 2006, vol. 71, pp. 455-462.

Database Genbank [online], Accession No. 034374, <http://www.ncbi.nlm.nih.gov/entrez/viewer.fcgi?6226478:PROT: 5142745>Jul. 10 uploaded, [retrieved on Oct. 10, 2008], Rivolta C. et al., Definition: Putative cytochrome P450 yjiB.

Mouri, T., et al., "A recombinant *Escherichia coli* whole cell biocatalyst harboring a cytochrom P450cam monooxygenase system coupled with enzymatic cofactor regeneration," Appl Microbiol. Biotechnol., vol. 72, pp. 514-520 (2006).

Tosha, T., et al., "L358P Mutation on Cytochrome P450cam Simulates Structural Changes upon Putidaredoxin Binding," J. Biolog. Chem., vol. 279, No. 41, pp. 42836-42843 (2004).

*Primary Examiner* — Tekchand Saidha
*Assistant Examiner* — Md Younus Meah
(74) *Attorney, Agent, or Firm* — Birch, Stewart, Kolasch & Birch, LLP

(57) ABSTRACT

Disclosed is a method for producing a hydroxylated form of a compound having an adamantane skeleton, which is useful as an intermediate for functional resins and pharmaceutical products, with high yield and at low cost. Specifically, a hydroxylated form of a compound having an adamantane skeleton can be obtained by using cytochrome P450. More specifically, an N-(5-hydroxy-2-adamantyl)-benzamide derivative can be produced by hydroxylating an N-(2-adamantyl)-benzamide derivative.

9 Claims, No Drawings

METHOD FOR PRODUCING HYDROXYLATED ADAMANTANE USING CYTOCHROME P450

This application is a Divisional application which claims priority under 35 U.S.C. §120 of application Ser. No. 12/678, 281 filed on Mar. 15, 2010, now U.S. Pat. No. 8,383,381 which is the National Phase under 35 U.S.C. §371 of International Application No. PCT/JP2008 /067248 filed on Sept. 25, 2008, which claims priority under 35 U.S.C. §119(a)-(d) of Application Number 2007-250617 filed in Japan on Sept. 27, 2007. All of these applications are hereby incorporated by reference for all purposes.

TECHNICAL FIELD

The present invention relates to a method for producing an hydroxylated adamantane using cytochrome P450.

BACKGROUND ART

The hydroxylated adamantane is known as a monomer of a functional resin such as a photosensitive resin and the like in the photolithography field (Patent Document 1), or an inhibitor of 11beta-hydroxysteroid dehydrogenase type I (11βHSD1) in the field of medicines (Patent Document 2, page 27). In addition, a compound having an adamantyl group is known also as a DPPIV inhibitor. And, when these compounds are synthesized, a compound wherein a part of substituents of the hydroxylated adamantane is protected is useful as a synthesis intermediate from its reactivity.

A process for producing a hydroxylated adamantane derivative using a microorganism has been previously known. For example, a hydroxylated adamantane derivative protected with benzamide can be produced using in vivo conversion of *Beauveria sulfurescens* (Non-patent Document 1). In addition, regarding an adamantane derivative protected with phthalimide, it has been reported that a dihydroxy form can be produced by in vivo conversion of *Sporotrichum sulfurescens* (Non-patent Document 2).

Cytochrome P450 (hereinafter, also referred to as P450) is a generic name of protoheme-containing proteins exhibiting a specific absorption band (Soret band) at around 450 nm when it is reduced and carbon monoxide is bound thereto. P450 is bound to a microsome of many animal and plant tissues, fungi, and yeasts, or an internal membrane of mitochondria of a part of animal tissues. Additionally, it exists in a soluble form in certain bacteria or fungi.

P450 has various substrate specificities, and there are enzymes exhibiting very broad substrate specificity, which can utilize a variety of organic compounds as a substrate. On the other hand, there are enzymes having more restricted substrate specificity, which react only with relatively limited kinds of organic compounds. P450 is involved in biosynthesis of bioactive lipids such as cholesterol, steroid hormone, bile acid and active-type vitamin D, metabolism of bioactive lipids such as heme, fatty acid and eicosanoid, metabolism of exogenous chemical substances including drugs, and the like. As specific function of P450, it is known that P450 catalyzes a variety of reactions such as a hydroxylation reaction, an epoxidation reaction, a dealkylation reaction, a denitrification reaction and the like of xenobiotic in cells expressing the P450.

Some P450s derived from microorganisms such as fungi or bacteria are known that they serve for production of industrially useful substances, and a part thereof are actually utilized in industrial production of useful drugs. A representative example is to hydroxylate a 6β-position of compactin with an actinomycete, *Streptomyces carbophilus*, and obtain pravastatin which is an antihyperlipemic agent, as a product (Non-patent Document 3, Patent Document 3). A process for producing active-type vitamin $D_3$ by hydroxylating a 1α-position and a 25-position of vitamin $D_3$ utilizing an actinomycete, *Pseudonocaria autotrophica* has been also put into practical use.

With respect to hydroxylation of adamantane, Non-patent Document 4 describes that adamantane is hydroxylated with P450cam, which is P450 of *Pseudomonas putida*. In addition, Non-patent Document 5 describes that five microorganisms hydroxylating adamantane were screened from 470 microorganisms, and suggests that P450 is involved in hydroxylation of adamantane in *Streptomyces griseoplanus*, which is one of those microorganisms.

However, none of documents describe or suggest hydroxylation of a compound having an adamantane skeleton using P450, for example, hydroxylation of an N-(2-adamantyl)-benzamide derivative using P450.

[Patent Document 1] Japanese Patent Application Laid-Open (JP-A) No. 2006-63061
[Patent Document 2] WO04/056744
[Patent Document 3] JP-A No. 6-70780
[Non-patent Document 1] Journal of Organic Chemistry, 1992, vol. 57, p. 7209-7212
[Non-patent Document 2] The Journal of Organic Chemistry, 1968, vol. 33, p. 3201-3207
[Non-patent Document 3] Gene, 1995, vol. 163, p. 81-85
[Non-patent Document 4] Archives of Biochemistry and Biophysics, 1984, vol. 228, p. 493-502
[Non-patent Document 5] Applied Microbiology and Biotechnology, 2006, vo. 71, p. 502-504

DISCLOSURE OF THE INVENTION

Problems to be Solved by the Invention

Object of the present invention is to provide a high-yield and stable process using P450 for producing a hydroxylated form of a compound having an adamantane skeleton which is a raw material of monohydroxy-2-adamantanamine useful as an intermediate of functional resins and medicines (e.g. N-(5-hydroxy-2-adamantyl)-benzamide derivative).

Means to Solve the Problems

The present inventors have intensively studied and, as a result, found out a method for hydroxylating an adamantane part of a compound having an adamantane skeleton using CYP109B1 which is one of P450s. More particularly, it was first found out that an N-(5-hydroxy-2-adamantyl)-benzamide derivative can be produced from an N-(2-adamantyl)-benzamide derivative. In addition, it was found out that productivity of an N-(5-hydroxy-2-adamantyl)-benzamide derivative can be increased by using a CYP109B1 mutant, 109FK, or a 109FK mutant, obtained by altering CYP109B1. In addition, it was found out that the resulting N-(5-hydroxy-2-adamantyl)-benzamide derivative is Anti isomoer at 100% which is preferable as an intermediate of medicines.

That is, the present invention relates to the following:
(1) A process for producing an N-(5-hydroxy-2-adamantyl)-benzamide derivative characterized by hydroxylating an N-(2-adamantyl)-benzamide derivative using cytochrome P450.

(2) The process of (1), wherein cytochrome P450 is a protein consisting of an amino acid sequence of SEQ ID No: 1 or 3, or a protein consisting of an amino acid sequence in which one to several amino acids are deleted, substituted, or added in the amino acid sequence, and having hydroxylation activity.

(3) The process of (1), wherein cytochrome P450 is a protein consisting of an amino acid sequence having one to several mutations selected from the group consisting of I77F, L357P, A362T, F41L, I77W, M105I, T234A, F232I, F232L and F232M in the amino acid sequence of SEQ ID No: 1, or a protein consisting of an amino acid sequence having one to several mutations selected from the group consisting of I77F, I77W, M105I, A196D, F232I, F232L, F232M, T234A, T244A, V399E and K702E in the amino acid sequence of SEQ ID No: 3.

(4) The process of (1), wherein the N-(2-adamantyl)-benzamide derivative is a compound of the formula:

[Formula 1]

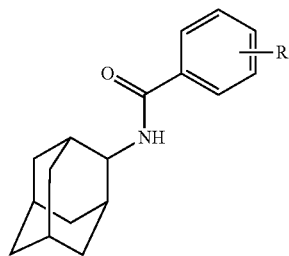

wherein R is hydrogen or a hydrophilic group.

(5) The process of (1), wherein the N-(5-hyhdroxy-2-adamantyl)-benzamide derivative is a compound of the formula:

[Formula 2]

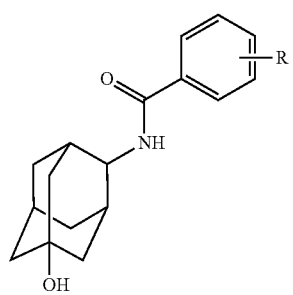

wherein R is hydrogen or a hydrophilic group.

(6) A process for producing a compound of the formula:

[Formula 3]

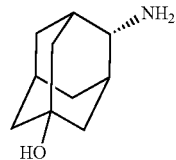

characterized by obtaining an N-(5-hyhdroxy-2-adamantyl)-benzamide derivative by the process of any one of (1) to (5), and deprotecting it.

(7) The process of (6), characterized in that the N-(5-hyhdroxy-2-adamantyl)-benzamide derivative is not isolated.

(8) A process for producing a compound of the formula (III):

[Formula 4]

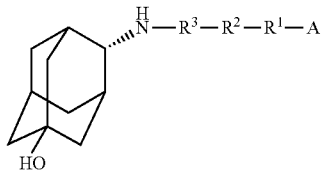

characterized by obtaining a compound of (I) by the process of (6) or (7), and reacting with a compound of the formula (II):

A-R$^1$—R$^2$—R$^3$—X wherein A is an optionally substituted cyclic hydrocarbon group or an optionally substituted heterocyclic group, R$^1$ is a single bond, —C(=O)—, —O— or NR$^{4-}$, R$^2$ is a single bond or optionally substituted alkylene, R$^3$ is a single bond or C(=O)—, X is a hydroxy group, halogen or a leaving group derived from a hydroxy group, and R$^4$ is hydrogen or optionally substituted alkyl.

(9) A method for hydroxylating an adamantane part of a compound having an adamantane skeleton, comprising using a protein consisting of an amino acid sequence of SEQ ID No: 1 or 3, or a protein consisting of an amino acid sequence in which one to several amino acids are deleted, substituted or added in the amino acid sequence, and having hydroxylation activity.

(10) A protein containing an amino acid sequence in which one to several amino acids are deleted, substituted or added in the amino acid sequence of SEQ ID No: 1, and having hydroxylation activity.

(11) A protein consisting of an amino acid sequence having one to several mutations selected from the group consisting of I77F, L357P, A362T, F41L, I77W, M105I, T234A, F232I, F232L and F232M in the amino acid sequence of SEQ ID No: 1.

(12) A protein consisting of the amino acid sequence of SEQ ID No: 3, or a protein containing an amino acid sequence in which one to several amino acids are deleted, substituted or added in the amino acid sequence, and having hydroxylation activity.

(13) A protein consisting of an amino acid sequence having one to several mutations selected from the group consisting of I77F, I77W, M105I, A196D, F232I, F232L, F232M, T234A, T244A, V399E and K702E in the amino acid sequence of SEQ ID No: 3.

(14) A compound of the formula:

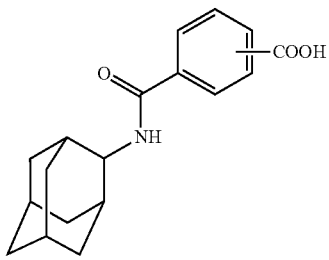

[Formula 5]

a salt or a solvate thereof.

(15) A compound of the formula:

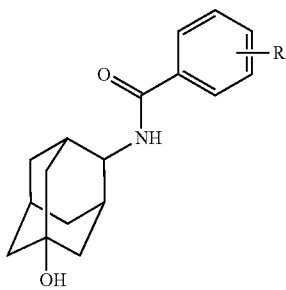

[Formula 6]

a salt or solvate thereof,
wherein R is hydrogen or a hydrophilic group.

Effect of the Invention

The method for hydroxylating an adamantane part of a compound having an adamantane skeleton of the present invention realizes stable production and supply, and enables effective, safe and low-cost production of a hydroxylated form of a compound having an adamantane skeleton.

BEST MODE FOR CARRYING OUT THE INVENTION

Terms used herein, unless otherwise indicated, are used in a sense normally used in the art. Terms which are particularly used herein will be explained below.

In the present invention, "cytochrome P450" is utilized as a catalyst for hydroxylating a compound having an adamantane skeleton. For example, it is utilized as a catalyst in a process for producing an N-(5-hydroxy-2-adamantyl)-benzamide derivative by hydroxylating an N-(-2-adamantyl)-benzamide derivative. Whether or not a protein which is P450 can be utilized as a catalyst for hydroxylating a compound having an adamantane skeleton can be determined, for example, by whether or not an N-(5-hydroxy-2-adamantyl)-benzamide derivative is obtained by action of the protein, or of the protein and a reducing system consisting of ferredoxin and reductase supplying an electron to the protein on an N-(2-adamantyl)-benzamide derivative which is a substrate. More particularly, a method for culturing a microorganism capable of expressing P450 in a suitable medium, and detecting the presence or absence of the N-(5-hydroxy-2-adamantyl)-benzamide derivative accumulated in the medium can be used. If necessary, by introducing a reducing system consisting of ferredoxin supplying an electron to P450 and reductase into a microorganism, the presence or absence can be more effectively detected. Detection of the N-(5-hydroxy-2-adamantyl)-benzamide derivative can be performed, for example, by high performance liquid chromatography (HPLC) using the N-(5-hydroxy-2-adamantyl)-benzamide derivative obtained by the present invention as a standard. Specifically, the method described in Examples later can be used. Examples of P450 useful in the present invention include CYP109B1, CYP101, CYP105D and the like, and a derivative thereof.

"Derivative" of P450 means a polypeptide having substantially the same biological function or activity as that of P450, that is, in the present invention, hydroxylation activity. A C-terminus of the polypeptide may be either of a carboxyl group, carboxylate, amide or ester. Examples include a fused protein with other protein, a modified entity obtained by adding a modifying group, a mutant obtained by deleting, substituting or adding an amino acid residue(s), and the like.

As "other protein" used in the fused protein, a protein that the fused protein exhibits substantially the same or more hydroxylation activity as that of P450 by fusing is preferable. Examples include R450Rhf reductase domain, P450BM3 reductase domain and the like.

Examples of the modifying group of the modified entity include a functional group exhibiting fluorescence property, a functional group which is not involved in formation of a steric structure of a polypeptide, and the like. Alternatively, it may be an amino acid residue other than amino acid residues constituting naturally occurring P450 (e.g. β-alanine and the like). Examples of the functional group exhibiting fluorescence property include eosin, fluorescein isothiocyanate (FITC) and the like. Examples of the functional group which is not involved in formation of a steric structure of a polypeptide include a spacer group, a representative of which is a β-alanine residue and the like. It is preferable that such a functional group is present at a terminal.

Examples of the mutant include a protein consisting of an amino acid sequence in which one to several amino acids are deleted, substituted or added in the amino acid sequence of P450, and having the function of P450, and the like.

Examples of the "amino acid sequence in which one to several amino acids are deleted, substituted or added" include (A) an amino acid sequence in which one or two or more (preferably, around 1 to 30, preferably around 1 to 10, and further preferably several (1 to 5)) amino acids in the amino acid sequence of P450 are deleted, (B) an amino acid sequence in which one or two or more (preferably, around 1 to 30, preferably around 1 to 10, and further preferably several (1 to 5)) amino acids in the amino acid sequence of P450 are substituted with other amino acids, (C) an amino acid sequence in which one or two or more (preferably, around 1 to 30, preferably around 1 to 10, and further preferably several (1 to 5)) amino acids are added in the amino acid sequence of P450, and (D) a protein containing an amino acid sequence which is a combination of them. When an amino acid sequence is deleted, substituted or added, a position of the deletion, substitution or addition is not particularly limited, provided that a mutant of P450 used in the present invention is a polypeptide having activity of catalyzing hydroxylation of a compound having an adamantane skeleton, even though an amino acid(s) is deleted, substituted or added. Examples include a polypeptide having at least 60% or more homology, preferably a polypeptide having 80% or more homology, and further preferably a polypeptide having 95% or more homology with the amino acid sequence of P450.

Herein, "CYP109B1" means a protein consisting of the amino acid sequence of SEQ ID No: 1.

"CYP109B1 mutant" means a protein containing an amino acid sequence in which one to several amino acids are deleted, substituted or added in the amino acid sequence of SEQ ID No: 1, and having hydroxylation activity. Examples include a protein consisting of an amino acid sequence having one to several mutations selected from the group consisting of I77F, L357P, A362T, F41L, I77W, M105I, T234A, F232I, F232L and F232M, in the amino acid sequence of SEQ ID No: 1. "One to several mutations" means around 1 to 5, preferably 1 to 3, and further preferably 1 or 2 mutations. Particularly, a protein consisting of an amino acid sequence having 1 to 5, and preferably 1 to 3 variations selected from the group consisting of I77F; I77F and L357P; I77F, M105I and T234A; and I77F and F232M, in the amino acid sequence of SEQ ID No: 1, is preferable.

"CYP109FK" means a protein consisting of the amino acid sequence of SEQ ID No: 3.

"CYP109FK mutant" means a protein containing an amino acid sequence in which one to several amino acids are deleted, substituted or added in the amino acid sequence of SEQ ID No: 3, and having hydroxylation activity. Examples include a protein consisting of an amino acid sequence having one to several mutations selected from the group consisting of I77F, I77W, M105I, A196D, F232I, F232L, F232M, T234A, T244A, V399E and K702E in the amino acid sequence of SEQ ID No: 3. "One to several mutations" means around 1 to 5, preferably 1 to 3, and further preferably 1 or 2 mutations. Particularly, a protein consisting of an amino acid sequence having 1 to 5, preferably 1 to 3 and particularly preferably one mutation selected from the group consisting of I77F, I77W, M105I, A196D, F232I, F232L, F232M, T234A, T244A, V399E and K702E in the amino acid sequence of SEQ ID No: 3, is preferable.

"Compound having an adamantane skeleton" includes any compound as far as it is a compound having an adamantane skeleton. Preferable examples include protected 2-aminoadamantane.

"Protected 2-aminoadamantane" includes any compound as far as it is a compound wherein an amino group of adamantanamine is protected. In this respect, a part other than a part to be hydroxylated, of an adamantane part may have a substituent. The substituent is not particularly limited, but examples thereof include halogen such as F, Cl, Br, I and the like, optionally substituted alkyl (e.g. unsubstituted alkyl and carbamoyl alkyl), hydroxy, alkoxy, nitro, aryl, arylalkyl, carboxy, ester (e.g. alkoxycarbonyl and the like), carbamoyl, alkenyl, alkynyl, carbamoyloxy, protected hydroxy (e.g. alkylhydroxy and the like) and the like. Preferable examples include an N-(2-adamantyl)-benzamide derivative, N-(2-adamantyl)-benzamide, N-(adamanan-2-yl)-phthalamic acid, N-(2-adamantyl)-p-methoxybenzyloxycarbonylamine and the like.

"N-(2-adamantyl)-benzamide derivative" means N-(2-adamantyl)benzamide or a derivative thereof. The derivative includes a compound wherein a benzene ring part is substituted with halogen, alkyl, hydroxy, alkoxy, nitro, aryl, arylalkyl, carboxy, ester, carbamoyl or the like, a compound wherein a part other than a part to be hydroxylated, of an adamantyl group is substituted with halogen, alkyl, hydroxy, alkoxy, nitro, aryl, arylalkyl, carboxy, ester, carbamoyl or the like, and a compound wherein a benzene ring part and an adamantane part are substituted with the aforementioned substituents. Preferable examples include a compound of the formula:

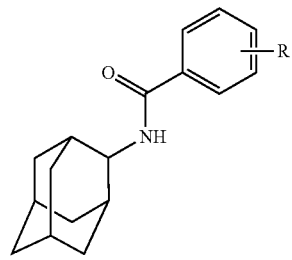

[Formula 7]

wherein R is hydrogen or a hydrophilic group.

"Hydrophilic group" is a group having strong affinity for water. That is, it refers to an atomic group which can form a weak bond with a water molecule by electrostatic interaction, a hydrogen bond or the like. Examples include —OH, —COOH, —NH$_2$, —OSO$_3$H, —SO$_3$H, —OPO$_3$H$_2$ and the like. Particularly, —COOH is preferable.

"N-(5-hydroxy-2-adamantyl)-benzamide derivative" means N-(5-hydroxy-2-adamantyl-1)-benzamide or a derivative thereof. Examples of the derivative also include a compound wherein a benzene ring is substituted with halogen, alkyl, hydroxy, alkoxy, nitro, aryl, arylalkyl, carboxy, alkoxycarbonyl, carbamoyl or the like. Preferable examples include a compound of the formula 8:

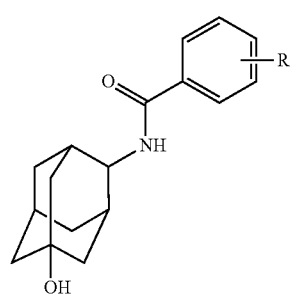

[Formula 8]

wherein R is hydrogen or a hydrophilic group. Further preferable examples include a compound of the formula 9:

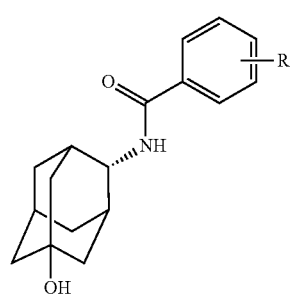

[Formula 9]

wherein R is hydrogen or a hydrophilic group.

A compound having an adamantane skeleton obtained by the present invention such as the N-(5-hydroxy-2-adamantyl)-benzamide derivative can be easily converted into monohydroxy-2-adamantanamine, that is, a compound of the formula:

[Formula 10]

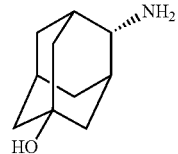

(I)

by removing a protecting group.

In addition, in the present invention, the N-(5-hydroxy-2-adamantyl)-benzamide derivative may or may not be isolated in a step of producing an N-(5-hydroxy-2-adamantyl)-benzamide derivative from an N-(2-adamantyl)-benzamide derivative and obtaining monohydroxy-2-adamantanamine by deprotection. Upon production of the N-(5-hydroxy-2-adamantyl)-benzamide derivative, the derivative can be once purified and deprotected. Alternatively, as described in Example 8, monohydroxy-2-adamantanamine can be obtained by performing deprotection while sterilization is conducted, without isolating the N-(5-hydroxy-2-adamantyl)-benzamide derivative.

Further, by reacting monohydroxy-2-adamantanamine obtained above with a compound of the formula (II): A-R$^1$—R$^2$—R$^3$—X wherein A is an optionally substituted cyclic hydrocarbon group or an optionally substituted heterocyclic group, R' is a single bond, —C(=O)—, —O— or NR$^4$—, R$^2$ is a single bond or optionally substituted alkylene, R$^3$ is a single bond or C(=O)—, X is a hydroxy group, halogen or a leaving group derived from a hydroxy group, and R$^4$ is hydrogen or optionally substituted alkyl, a compound of the formula (III):

[Formula 11]

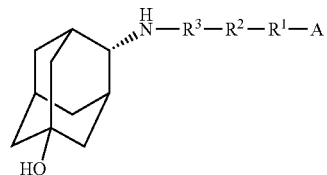

(III)

can be produced.

[Formula 12]

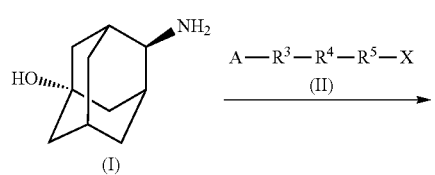

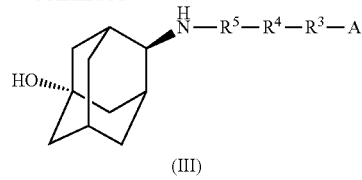

(III)

This is a step of reacting a compound of the formula (I) and a compound of the formula (II) to produce a compound of the formula (III).

Examples of a solvent include N-dimethylformamide, dimethyl sulfoxide, aromatic hydrocarbons (e.g. toluene, benzene, xylene and the like), saturated hydrocarbons (e.g. cyclohexane, hexane and the like), halogenated hydrocarbons (e.g. dichloromethane, chloroform, 1,2-dichloroethane and the like), ethers (e.g. tetrahydrofuran, diethyl ether, dioxane, 1,2-dimethoxyethane and the like), esters (e.g. methyl acetate, ethyl acetate and the like), ketones (e.g. acetone, methyl ethyl ketone and the like), nitriles (e.g. acetonitrile and the like), alcohols (e.g. methanol, ethanol, isopropanol, tert-butanol and the like), water, a mixed solvent thereof and the like. Preferable are halogenated hydrocarbons (e.g. dichloromethane, chloroform, 1,2-dichloroethane and the like), nitriles (e.g. acetonitrile and the like), ethers (e.g. tetrahydrofuran, diethyl ether, dioxane, 1,2-dimethoxyethane and the like), alcohols (e.g. methanol, ethanol, isopropanol, tert-butanol and the like), water and the like.

Without any limitation, preferable are N,N-dimethylformamide, dimethyl sulfoxide, xylene, dichloromethane, chloroform, 1,2-dichloroethane, diethyl ether, dioxane, 1,2-dimethoxyethane, acetonitrile, methanol, ethanol, isopropanol, tert-butanol, toluene, tetrahydrofuran and water.

Further preferable are dichloromethane, methanol, and ethanol.

When R$^5$ is —C(=O)— and X is a hydroxy group, a condensing agent and a base can be used in the step. As the condensing agent, for example, 1,1-carbonyldiimidazole, dicyclohexylcarbodiimide, water-soluble carbodiimide (1-ethyl-3-(3'-dimethylaminopropyl)carbodiimide) or the like can be used. Examples of the base include metal hydrides (e.g. sodium hydride and the like), metal hydroxides (e.g. sodium hydroxide, potassium hydroxide, lithium hydroxide, barium hydroxide and the like), metal carbonates (e.g. sodium carbonate, calcium carbonate, cesium carbonate and the like), metal alkoxides (e.g. sodium methoxide, sodium ethoxide, potassium tert-butoxide and the like), sodium bicarbonate, metal sodium, organic amines (e.g. triethylamine, diisopropylethylamine, DBU, 2,6-lutidine and the like) and the like.

When R$^5$ is —C(=O)— and X is halogen, the above base can be used in the step.

When R$^3$ is —C(=C)—, R$^4$ is optionally substituted alkylene, R$^5$ is a single bond and X is halogen or a leaving group derived from a hydroxy group, the above base can be used in the step.

Reaction conditions are not particularly limited, but the substances may be stirred at about −20 to 100° C., and preferably about −10 to 80° C. for usually 1 hour to 36 hours, and preferably 1 hour to 24 hours.

The thus obtained Compound (III) is useful as an 11β-hydroxysteroid dehydrogenase inhibitor, a Dipeptidyl Peptidase IV (DPP IV) inhibitor, a Jak3 inhibitor or the like.

"Halogen" includes fluorine, chlorine, bromine and iodine.

"Alkyl" means C1 to C10 straight or branched alkyl. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl and the like. Preferable is C1 to C6 or C1 to C4 alkyl. Examples include methyl, ethyl, n-propyl, isopropyl, n-butyl, isobutyl, sec-butyl, tert-butyl, n-pentyl, isopentyl, neopentyl, n-hexyl and isohexyl.

An alkyl part of "alkoxy" or "alkoxycarbonyl" has the same meaning as the above alkyl.

Examples of "aryl" include monocyclic aromatic hydrocarbon groups (e.g. phenyl) and polycyclic aromatic hydrocarbon groups (e.g. 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like).

"Arylalkyl" means the above alkyl substituted with the above aryl.

"Cyclic hydrocarbon group" includes "cycloalkyl", "cycloalkenyl" and "aryl".

"Cycloalkyl" means C3 to C15 cyclic saturated hydrocarbon group. Examples include cyclopropyl, cyclobutyl, cyclopentyl, cyclohexyl, cycloheptyl, cyclooctyl, a bridged cyclic hydrocarbon group, a Spiro hydrocarbon group and the like.

"Bridged cyclic hydrocarbon group" includes a group obtained by removing one hydrogen from C5 to C8 aliphatic ring in which two or more rings share 2 or more atoms. Examples include bicyclo[2.1.0]pentyl, bicyclo[2.2.1]heptyl, bicyclo[2.2.2]octyl and bicyclo[3.2.1]octyl, tricyclo[2.2.1.0]heptyl and the like.

"Spiro hydrocarbon group" includes a group obtained by removing one hydrogen from a ring in which two hydrocarbon rings are constructed by sharing one carbon atom. Examples include spiro[3.4]octyl and the like.

"Cycloalkenyl" means C3 to C7 cyclic unsaturated aliphatic hydrocarbon group. Examples include cyclopropenyl, cyclobutenyl, cyclopentenyl, cyclohexenyl, and cycloheptenyl. Preferable are cyclopropenyl, cyclobutenyl, cyclopentenyl, and cyclohexenyl. Cycloalkenyl includes a bridged cyclic hydrocarbon group and a spiro hydrocarbon group having an unsaturated bond in a ring.

"Heterocyclic group" includes "heteroaryl and heterocycle".

"Heteroaryl" means a monocyclic aromatic heterocyclic group and a fused aromatic heterocyclic group. The monocyclic aromatic heterocyclic group means a group derived from a 5- to 8-membered aromatic ring optionally containing 1 to 4 of oxygen, sulfur and/or nitrogen atoms in a ring, optionally having a bond at an arbitrary replaceable position. The fused aromatic heterocyclic group means a group in which a 5- to 8-membered aromatic ring optionally containing 1 to 4 of oxygen, sulfur and/or nitrogen atoms in a ring is fused with 1 to 4 of a 5- to 8-membered aromatic carbocycle or other 5- to 8-membered aromatic heterocycle, and optionally having a bond at an arbitrary replaceable position. Examples include furyl (e.g. 2-furyl and 3-furyl), thienyl (e.g. 2-thienyl and 3-thienyl), pyrrolyl (e.g. 1-pyrrolyl, 2-pyrrolyl and 3-pyrrolyl), imidazolyl (e.g. 1-imidazolyl, 2-imidazolyl and 4-imidazolyl), pyrazolyl (e.g. 1-pyrazolyl, 3-pyrazolyl and 4-pyrazolyl), triazolyl (e.g. 1,2,4-triazol-1-yl, 1,2,4-triazol-3-yl and 1,2,4-triazol-4-yl), tetrazolyl (e.g. 1-tetrazolyl, 2-tetrazolyl and 5-tetrazolyl), oxazolyl (e.g. 2-oxazolyl, 4-oxazolyl and 5-oxazolyl), isoxazolyl (e.g. 3-isoxazolyl, 4-isoxazolyl and 5-isoxazolyl), thiazolyl (e.g. 2-thiazolyl, 4-thiazolyl and 5-thiazolyl), thiadiazolyl, isothiazolyl (e.g. 3-isothiazolyl, 4-isothiazolyl and 5-isothiazolyl), pyridyl (e.g. 2-pyridyl, 3-pyridyl and 4-pyridyl), pyridazinyl (e.g. 3-pyridazinyl and 4-pyridazinyl), pyrimidinyl (e.g. 2-pyrimidinyl, 4-pyrimidinyl and 5-pyrimidinyl), furazanyl (e.g. 3-furazanyl), pyrazinyl (e.g. 2-pyrazinyl), oxadiazolyl (e.g. 1,3,4-oxadiazol-2-yl), benzofuryl (e.g. 2-benzo[b]furyl, 3-benzo[b]furyl, 4-benzo[b]furyl, 5-benzo[b]furyl, 6-benzo[b]furyl and 7-benzo[b]furyl), benzothienyl (e.g. 2-benzo[b]thienyl, 3-benzo[b]thienyl, 4-benzo[b]thienyl, 5-benzo[b]thienyl, 6-benzo[b]thienyl and 7-benzo[b]thienyl), benzimidazolyl (e.g. 1-bemzimidazolyl, 2-bemzimidazolyl, 4-benzimidazolyl and 5-benzimidazolyl), dibenzofuryl, benzoxazolyl, quinoxalyl (e.g. 2-quinoxalyl, 5-quinoxalyl and 6-quinoxalyl), cinnolinyl (e.g. 3-cinnolinyl, 4-cinnolinyl, 5-cinnolinyl, 6-cinnolinyl, 7-cinnolinyl and 8-cinnolinyl), quinazolyl (e.g. 2-quinazolyl, 4-quinazolyl, 5-quinazolyl, 6-quinazolyl, 7-quinazolyl and 8-quinazolyl), quinolyl (e.g. 2-quinolyl, 3-quinolyl, 4-quinolyl, 5-quinolyl, 6-quinolyl, 7-quinolyl and 8-quinolyl), phthalazinyl (e.g. 1-phthalazinyl, 5-phthalazinyl and 6-phthalazinyl), isoquinolyl (e.g. 1-isoquinolyl, 3-isoquinolyl, 4-isoquinolyl, 5-isoquinolyl, 6-isoquinolyl, 7-isoquinolyl and 8-isoquinolyl), puryl, pteridinyl (e.g. 2-pteridinyl, 4-pteridinyl, 6-pteridinyl and 7-pteridinyl), carbazolyl, phenanthrydinyl, acridinyl (e.g. 1-acridinyl, 2-acridinyl, 3-acridinyl, 4-acridinyl and 9-acridinyl), indolyl (e.g. 1-indolyl, 2-indolyl, 3-indolyl, 4-indolyl, 5-indolyl, 6-indolyl and 7-indolyl), isoindolyl, phenazinyl (e.g. 1-phenazinyl and 2-phenazinyl), phenothiazinyl (e.g. 1-phenothiazinyl, 2-phenothiazinyl, 3-phenothiazinyl and 4-phenothiazinyl) and the like.

"Heterocycle" means a non-aromatic heterocyclic group optionally containing 1 to 4 of oxygen, sulfur and/or nitrogen atoms in a ring, and optionally having a bond at an arbitrary replaceable position. In addition, such a non-aromatic heterocyclic group may be further bridged with C1 to C4 alkyl chain, and may be fused with cycloalkane (5- to 6-membered ring is preferable) or a benzene ring. Heterocycle may be saturated or unsaturated as far as it is non-aromatic. Examples include 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrzolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl and the like.

"Alkylene" includes a divalent group in which 1 to 6 methylenes are continuous. Examples include methylene, ethylene, trimethylene, tetramethylene, pentamethylene, hexamethylene and the like.

Examples of "leaving group derived from a hydroxy group" include -Oms, -OTs, -OTf, -ONs and the like. Herein, "Ms" represents a methanesulfonyl group, "Ts" represents a paratoluenesulfonyl group, "Tf" represents a trifluoromethanesulfonyl group, and "Ns" represents an orthonitrobenzenesulfonyl group.

A in the formula (II) and the formula (III) is preferably an optionally substituted heterocyclic group. Further preferable examples include optionally substituted heteroaryl and optionally substituted heterocycle. More preferable examples include furan, thiophene, pyrrole, pyrazole, triazole, oxazole, thiazole, isothiazole, pyridine, morpholine, piperidine, piperazine, pyrrolidine, tetrahydrothiophene, benzoxazine, benzofuran, and pyrrolopyridine. Without any limitation, particularly, isoxazole and pyrazole are preferable. Examples of A include an optionally substituted cyclic hydrocarbon group. Preferable is phenyl.

Examples of the substituent include —$OR^5$, —$SR^5$, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group of the formula: —CH═CH—C($R^aR^b$)—$R^c$—$R^d$, a group of the formula: —C($R^eR^f$)$_m$—C($R^aR^b$)—$R^c$—$R^d$ and the like.

$R^a$ and $R^b$ are each independently hydrogen, optionally substituted alkyl or halogen, or $R^a$ and $R^b$ may be taken together with an adjacent carbon atom to form an optionally substituted ring, $R^c$ is —(CH$_2$)$_n$—, wherein n is a integer of 0 to 3, $R^d$ is hydrogen, halogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group of the formula: —C(═O)—NR$^g$R$^h$ or a group of the formula: —NR$^i$R$^j$, $R^e$ and $R^f$ are each independently hydrogen, halogen or optionally substituted alkyl, $R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxy, or optionally substituted carbamoyl, or $R^g$ and $R^h$ may be taken together with an adjacent nitrogen atom to form an optionally substituted ring, $R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, or optionally substituted sulfamoyl, or $R^i$ and $R^j$ may be taken together with an adjacent nitrogen atom to form an optionally substituted ring, $R^5$ is optionally substituted alkyl, optionally substituted alkenyl, optionally substituted cycloalkyl, optionally substituted aryl, optionally substituted heteroaryl, or optionally substituted heterocycle, and m are each independently an integer of 1 to 3.

$R^1$ is preferably a single bond.
$R^2$ is preferably a single bond.
$R^3$ is preferably —C(═O)—.
X is preferably a hydroxy group.

Details of compounds of the formula (II) and the formula (III), and a process for preparing them are collectively described in WO2006/132197, WO2007/058346, PCT/JP2007/056538, and Japanese Patent Application No. 2007-132259.

A method for hydroxylating a compound having an adamantane skeleton of the present invention, for example, a process for producing an N-(5-hydroxy-adamantan-2-yl)-benzamide derivative by hydroxylating an N-(2-adamantyl)-benzamide derivative (hereinafter, referred to as "present process" in some cases) characterized by using P450 having hydroxylation activity (hereinafter, referred to as "present protein" in some cases) as a catalyst. Specifically, the present process includes a step of acting at least one of (a) the present protein, or
the present protein and a reduction system consisting of ferredoxin and reductase supplying an electron to the protein, or
(b) a microorganism capable of expressing the present protein, on an N-(2-adamantyl)-benzamide derivative which is a substrate, to selectively hydroxylate an adamantane part.

(a) Present Protein

The present protein can be made by obtaining and utilizing a polynucleotide encoding the protein (hereinafter, referred to as "present gene" in some cases). A method for obtaining the present gene and a process for producing the present protein (a process for making an expression vector or a transformant and the like) will be specifically described below.

(1) Method for Obtaining Present Gene

Present gene can be obtained from *Bacillus subtilis* by making a cDNA library by a conventional method.

Examples of the process for making a cDNA library include the methods described in Molecular Cloning: A Laboratory Manual, Second Edition (1989) (Cold Spring Harbor Laboratory Press), Current Protocols in Molecular Biology (1994) (Wiley-Interscience), DNA Cloning 1: Core Techniques, A Practical Approach, Second Edition (1995) (Oxford University Press) and the like, and a method using a commercially available kit such as SuperScript Plasmid System for cDNA Synthesis and Plasmid Cloning (Invitrogen), ZAP-cDNA Synthesis Kits (Stratagene) and the like.

Examples of a cDNA obtained by the methods include a DNA encoding a protein consisting of an amino acid sequence of SEQ ID No: 1, specifically, a DNA consisting of a base sequence of SEQ ID No: 2 and the like. The cDNA can be used for making an expression plasmid in which the present gene is incorporated into a suitable expression vector. The expression vector, a method for using the expression plasmid and the like will be described in "Process for producing present protein" later.

Alternatively, a DNA can be also prepared by chemically synthesizing a DNA encoding the present protein based on an amino acid sequence. Chemical synthesis of a DNA can be performed by a DNA synthesizer manufactured by Shimadzu Corporation utilizing a thiophosphite method, a DNA synthesizer model 392 manufactured by Perkin Elmer utilizing a phosphoamidite method, or the like.

Further, an objective DNA can be also prepared by performing PCR using oligonucleotides as a sense primer and an antisense primer based on an amino acid sequence and a cDNA prepared from a mRNA of cells expressing a mRNA complementary with these DNAs as a template.

(2) Process for Producing Present Protein

The present protein can be produced by expressing a polynucleotide encoding the present protein in a host cell, for example, by the methods described in Molecular Cloning: A Laboratory Manual, Second Edition (1989) (Cold Spring Harbor Laboratory Press), Current Protocols in Molecular Biology (1994) (Wiley-Interscience) and the like, as below.

As the host cell, any of a prokaryotic cell, yeast, an animal cell, a plant cell, an insect cell and the like can be used as far as it can express an objective gene. As an expression vector, an expression vector which can be autonomously replicated in the above host cell, or can be incorporated into a chromosome, and contains a promoter at a position suitable for transcription of the present protein is used.

(i) Case where Prokaryote is Used as Host

It is preferable that the expression vector of the present protein can be autonomously replicated in a prokaryote and, is composed of a promoter, a ribosome binding sequence, a DNA encoding the present polypeptide and a transcription terminator sequence. A gene for controlling a promoter may be contained.

Examples of the expression vector include pBTrp2, pBTac1, pBTac2 (Roche Diagnostics), Bluescript II SK (+), pBluescript II SK (−) (Stratagene), pSKV28, pUC118, pUC19 (Takara Shuzo Co., Ltd.), pKK233-2 (GE Healthcare), pSE280, pSupex, pUB110, pTP5, pC194, pTixFus (Invitrogen), pGEMEX-1 (Promega), pQE-8 (Qiagen), pGEX (GE Healthcare), pET system (Novagen), pMAL-c2 (New England Biolabs), pKYP10 (JP-A No. 58-110600), pKYP200 (Agricultural Biological Chemistry, 48, 669 (1984)), pLSA1 (Agricultural Biological Chemistry, 53,277 (1989)), pGEL1 (Proceeding of the National Academy of Sciences USA, 82, 4306 (1985)), pEG400 (Journal of Bacteriology, 172, 2392 (1990)), pTrs30 (FERM BP-5407), pTrs32 (FERM BP-5408), pGHA2 (FERM BP-400), pGKA2 (FERM B-6798), pPA1 (JP-A No. 63-233798), pTerm2 (JP-A No. 3-22979, U.S. Pat. Nos. 4,686,191, 4,939,094 and 5,160,735) and the like.

As the promoter, any promoter can be used as far as it can be expressed in a host cell such as *Escherichia coli* and the like. Examples include promoters derived from *Escherichia coli* and phage such as trp promoter (Ptrp), lac promoter (P lac), PL promoter, PR promoter, PSE promoter and the like, SPO1 promoter, SPO2 promoter, penP promoter and the like. Alternatively, artificially designed and altered promoters such as a promoter in which two Ptrp(s) are connected in series (Ptrpx2), tac promoter, lacT7 promoter, and 1etI promoter can be also used.

It is preferable to use a plasmid in which a length between a Shine-Dalgarno sequence being a ribosome binding sequence and an initiation codon is adjusted at a suitable distance, for example, 6 to 18 bases. A transcription terminator sequence is not necessarily required for expression of the present gene, but it is preferable to arrange a transcription terminator sequence immediately downstream of a structural gene.

Examples of the host cell include prokaryotes such as genus *Escherichia*, *Serratia*, *Bacillus*, *Brevibacterium*, *Corynebacterium*, *Microbacterium*, *Pseudomonas* and the like. Examples of genus *Escherichia* include strains of *E. coli* XL1-Blue, XL2-Blue, DH1, MC1000, KY3276, W1485, JM109, HB101, No. 49, W3110, NY49, BL21, BL21 (DE3), BL21 (DE3) pLysS, HMS174 (DE3), HMS174 (DE3) pLysS and the like. Examples of genus *Serratia* include strains of *S. ficaria, S. fonticola, S. liquefaciens, S. marcescens* and the like. Examples of genus *Bacillus* include strains of *B. subtilis, B. amyloliquefaciens* and the like. Examples of genus *Brevibacterium* include strains of *B. ammoniagenes, B. immariophilum* (ATCC:14068), *B. saccharolyticum* (ATCC:14066) and the like. Examples of genus *Corynebacterium* include strains of *C. glutamicum* (ATCC:13032), *C. glutamicum* (ATCC14067), *C. glutamicum* (ATCC13869), *C. acetoacidophilum* (ATCC13870) and the like. Examples of genus *Microbacterium* include strains of *M. ammoniaphilum* (ATCC: 15354) and the like. Examples of genus *Pseudomonas* include strains of *P. mephitica* and the like.

As a method for introducing a recombinant vector, any method can be used as far as it is a method for introducing a DNA in the above host cell. Examples include an electroporation method (Nucleic Acids Research, 16, 6127 (1988)), a Calcium Phosphate Method (Proceedings of the National Academy of Sciences USA, 69, 2110 (1972)), a Protoplast Method (JP-A No. 63-1483942), methods described in Gene, 17, 107 (1982) and Molecular & General Genetics, 168, 111 (1979) and the like.

(ii) Case where Yeast is Used as Host

When yeast is used as a host, examples of an expression vector include Yep13 (ATCC: 37115), Yep24 (ATCC: 37051), YCp50 (ATCC: 37419), pHS19, pHS15 and the like.

As the promoter, any promoter can be used as far as it can be expressed in yeast. Examples include ADH1 (alcohol dehydrogenase) promoter, PHO5 (acidic phosphatase) promoter, PGK1 (phosphoglycerate kinase) promoter, GAPDH (glyceraldehyde 3-phosphate dehydrogenase) promoter, GAL1 (galactose kinase) promoter, GAL10 (UDP galactose 4-epimerase) promoter, MFα1 (α pheromone) promoter, CUP1 (metallothionein) promoter and the like.

Examples of the host include *Saccharomyces cerevisiae, Schizosaccharomyces pombe, Kluyveromyces lactis, Trichosporon pullulans, Schwanniomyces alluvius Pichia pastoris* and the like.

As the method for introducing a recombinant vector, any method can be used as far as it is a method for introducing a DNA into a host. Examples include an electroporation method (Methods in Enzymology, 194, 182 (1990)), a Spheroplast Method (Proceedings of the National Academy of Sciences USA, 84, 1929 (1978)), a Lithium Acetate Method (Journal of Bacteriology, 153, 163 (1983)), the methods described in Proceedings of the National Academy of Sciences USA, 75, 1929 (1978)) and the like.

(iii) Case where Animal Cell is Used as Host

When an animal cell is used as a host, examples of an expression vector includes pcDNA1/Amp, pcDNA1, pCDM8, pREP4 (Invitrogen), pAGE107 (Cytotechnology, 3, 133 (1990)), pAGE103 (The Journal of Biochemistry, 101, 1307 (1987)), pAMo, pAMoA (pAMoPRSA) (The Journal of Biological Chemistry, 268, 22782-22787 (1993)), pAS3-3 (JP-A No. 2-22705) and the like.

As a promoter, any promoter can be used as far as it can be expressed in a host. Examples include IE (Immediate-early) gene promoter of human cytomegalovirus (hCMV), SV40 early promoter, a long terminal repeat promoter of Moloney Murine Leukemia Virus, a retrovirus promoter, HSP promoter, SRα promoter, a metallothionein promoter and the like. Alternatively, an enhancer of an IE gene of human CMV may be used together with a promoter.

Examples of an animal cell used in a host include a human-derived strain cell such as HEK298 (human fatal kidney cell, ATCC: CRL-1573), Namalwa (Burkitt's lymphoma, ATCC: CRL-1432), HeLa (uterine cervical cancer cell, ATCC: CCL-2), HBT5637 (leukemia cell, JP-A No. 63-299), BALL-1 (leukemia cell) and HCT-15 (large intestine cancer cell), a mouse-derived strain cell such as Sp2/0-Ag14 (mouse myeloma cell, ATCC: CRL-1581) and NSO (mouse myeloma cell), a monkey-derived strain cell such as COS-1 (African Green Monkey kidney cell (SV40 transformant cell), ATCC: CRL-1650) and COS-7 (African Green Monkey kidney cell (SV40 transformant cell), ATCC: CRL-1651), a hamster-derived strain cell such as CHO-K1 (Chinese hamster ovary cell, ATCC: CCL-61) and BHK-21 (C-13) (Sicilian hamster young kidney cell, ATCC: CCL-10), a rat-derived strain such as cell PC12 (adrenal melanocytoma, ATCC: CRL-1721) and YB2/0 (rat myeloma cell, ATCC: CRL-1662) and the like.

As a method for introducing a recombinant vector, any method can be used as far as it is a method for introducing a DNA into a host. Examples include an electroporation method (Cytotechnology, 3, 133, (1990)), a calcium phosphate method (JP-A No. 2-22705), a lipofection (Proceedings of the National Academy of Sciences USA, 84, 7413 (1987)), Virology, 52, 456 (1973)).

(iv) Case where Plant Cell is Used as Host

When a plant cell or a plant individual is used as a host, a polypeptide can be produced according to the known method (Tissue Culture, 20 (1994), Tissue Culture 21 (1995), Trends in Biotechnology, 15, 45 (1997)). Examples of an expression vector include Ti plasmid, a tobacco mosaic virus vector and the like. As a promoter used in gene expression, any promoter can be used as far as it can be expressed in a plant cell. Examples include a cauliflower mosaic virus (CaMV) 35S promoter, a rice actin 1 promoter and the like. In addition, an efficiency of gene expression can be increased by inserting intron 1 of an alcohol dehydrogenase gene of corn or the like between a promoter and a gene to be expressed.

Examples of a host include plant cells such as potato, tobacco, corn, rice, rapeseed, soybean, tomato, carrot, wheat, barley, rye, alfalfa, flax and the like.

As a method for introducing a recombinant vector, any method can be used as far as it is a method for introducing a DNA into a host. Examples include a method using *Agrobacterium* (JP-A No. 59-140885, JP-A No. 60-70080 and WO 94/00977), an electroporation method (JP-A No. 60-251887), a particle gun (gene gun) method (Japanese Patent No. 2606856 and Japanese Patent No. 2517813) and the like.

(v) Case where Insect Cell is Used as Host

When an insect cell is used as a host, examples of a transfer vector include pVL1392, pVL1393, pBlueBacIII (Invitrogen) and the like. Examples of a virus for infection include baculovirus which infects Hadeninae insects, *Autographa california* nuclear polyhedrosis virus (AcMNPY) Bac-N-Blue DNA and the like. Examples of a method for transforming an insect cell include the methods described in Baculovirus Expression Vector: A Laboratory Manual (1992) (W. H. Freeman and Company), Molecular Cloning: A Laboratory Manual, Second Edition (1989) (Cold Spring Harbor Laboratory Press), Current Protocols in Molecular Biology (1994) (Wiley-Interscience), BioTechnology, 6, 47 (1988) and the like.

A polypeptide can be expressed by adding a transfer vector containing an objective gene, and a baculovirus DNA for infecting an insect cell to an insect cell culture solution to infect the insect cell with a virus expressing an objective gene obtained by recombination.

Examples of the insect cell used as a host include a strain cell derived from *Spodoptera frugiperda* (cabbage armyworm) or *Trichoplusia ni* (nettle), and the like. Examples of the cell derived from *S. frugiperda* include Sf9 (ATCC: CRL-1711, ovary cell), Sf21 (ovary cell) and the like. Examples of the cell strain derived from *T. ni* include High Five, BTI-TN-5B1-4 (ovary cell, Invitrogen) and the like.

As a method for introducing a recombinant vector, any method can be used as far as it is a method which can introduce the vector into a host. Examples include a calcium phosphate method (JP-A No. 2-22705), a lipofection method (Proceedings of the National Academy of Sciences USA, 84, 7413 (1987)) and the like. In addition, as in the animal cell, an electroporation method (Cytotechnology, 3, 133 (1990)) and the like can be also used.

(vi) Culturing Method

When a transformant harboring a recombinant vector with a DNA encoding the present protein incorporated therein is a cell such as *Escherichia coli*, yeast, an animal cell a plant cell or the like, a cell is cultured according to a conventional culturing method suitable for various hosts, the protein is made to be produced and accumulated, and the protein is recovered from a transformant or a culture solution, thereby, the protein can be produced. When a transformant is an animal or plant individual, an individual is reared or cultivated according to a conventional growing method suitable for various hosts, the protein is made to be produced and accumulated, and the protein is recovered from the animal or plant individual, thereby, the protein can be produced.

When a host is an animal individual, for example, a non-human transgenic animal harboring the present gene is reared, the present protein encoded by the recombinant DNA is made to be produced and accumulated in the animal, and the protein is recovered from the animal individual, thereby, the present protein can be produced. Examples of a place of production and accumulation in an animal individual include milk, saliva, egg, and the like of the animal.

When a host is a plant individual, for example, a transgenic plant harboring a gene encoding the present protein is cultivated, the present protein encoded by the recombinant DNA is made to be produced and accumulated in the plant individual, and the polypeptide is recovered from the plant individual, thereby, the present protein can be produced.

When a host is a prokaryote such as *Escherichia coli* and the like, or a eukaryote such as yeast and the like, for example, a transformant harboring a gene encoding the present protein is cultured in a medium, the present protein encoded by the recombinant DNA is made to be produced and accumulated in a culture solution, and the protein is recovered from the culture solution, thereby, the present protein can be produced.

A method for culturing a transformant harboring a gene encoding the present protein in a medium can be performed according to a conventional method used in culturing a host.

As a medium for culturing the resulting transformant obtained by using a prokaryote such as *Escherichia coli* and the like or a eukaryote such as yeast and the like as a host, any of a natural medium and a synthetic medium may be used as far as it is a medium containing a carbon source, a nitrogen source, inorganic salts or the like which can be utilized by the organism, and which can effectively perform culturing of the transformant.

When a transformant is a prokaryote such as *Escherichia coli* and the like or a eukaryote such as yeast and the like, as a medium for culturing the resulting transformant, any of a natural medium and a synthetic medium may be used as far as it is a medium containing a carbon source, a nitrogen source, inorganic salts or the like which can be utilized by a host, and which can effectively perform culturing of the transformant. As a medium for culturing a transformant when a host is *Escherichia coli*, for example, a YT medium containing Bacto triptone, yeast extract and sodium chloride is preferable.

As the carbon source, a carbon source which can be utilized by each microorganism can be used. Examples include hydrocarbons such as glucose, fructose, sucrose, molasses containing them, starch, starch hydrolysate and the like, organic acids such as acetic acid, propionic acid and the like, and alcohols such as ethanol, propanol and the like.

As the nitrogen source, ammonia, various ammonium salts of inorganic or organic acids such as ammonium chloride, ammonium sulfate, ammonium acetate, ammonium phosphate and the like, other nitrogen-containing substances, peptone, meat extract, yeast extract, corn steep liquor, casein hydrolysate, soybean cake, soybean cake hydrolysate, various fermentation bacterial cells and digested substances thereof and the like can be used.

As the inorganic salt, primary potassium phosphate, secondary potassium phosphate, magnesium phosphate, magnesium sulfate, sodium chloride, ferrous sulfate, manganese sulfate, copper sulfate, calcium carbonate and the like can be used. Culturing is performed under the aerobic condition, such as shaking culturing, deep bubbling stirring culturing and the like.

A culturing temperature is suitably 15 to 40° C., and a culturing time is usually 5 hours to 7 days. pH during culturing is retained at 3.0 to 9.0. pH is adjusted with an inorganic or organic acid, an alkaline solution, urea, calcium carbonate, ammonia or the like. And, if necessary, an antibiotic such as ampicillin, tetracycline, kanamycin and the like may be added to a medium during culturing.

When a microorganism transformed with an expression vector using an inducible promoter as a promoter is cultured, if necessary, an inducer may be added to a medium. For example, when a transformant transformed with an expression vector using a lac promoter is cultured, isopropyl-β-D-thiogalactopyranoside or the like may be added to a medium. When a transformant transformed with an expression vector using a trp promoter is cultured, indoleacrylic acid or the like may be added to a medium. A cell or organ of a plant with a gene introduced therein can be cultured at a large scale using a jar fermenter. As a medium for culturing, a medium generally used such as a Murashige and Skoog (MS) medium, a White medium, a medium in which a plant hormone such as auxin, cytokinin and the like is added to these medium, or the like, can be used.

When a transformant for producing the present protein is an animal cell, as a medium for culturing the cell, a medium generally used such as a RPMI1640 medium (The Journal of the American Medical Association, 199, 519 (1967)), a MEM medium (Science, 130, 432 (1959)), a D-MEM medium (Virology, 8, 396 (1959)), a 199 medium (Proceedings of the Society for the Biological Medicine, 73, 1 (1950)), a medium in which bovine fetal serum (FCS) or the like is added to these medium, or the like, can be used.

Culturing is usually performed for 1 to 7 days under the condition such as pH 6 to 8, 25 to 40° C., the presence of 5% $CO_2$ and the like. In addition, if necessary, an antibiotic such as kanamycin, penicillin, streptomycin and the like may be added to a medium during culturing.

When a transformant is an insect cell, as a medium for culturing, a TNM-FH medium (Pharmingen), a Sf-900II SFM medium (Invitrogen), ExCell400, ExCell405 (JRH Bioscience), Grace's Insect Medium (Nature, 195, 788 (1962)) and the like can be used.

(vii) Process of Production

The present protein can be produced by culturing a transformant, and isolating/purifying the present protein from a culture solution. A method for isolating/purifying the present protein can be performed by a conventional method well-known in the art. For example, a method for isolating/purifying an enzyme or a method for purifying glucotransferase of Sandler et al. (Methods in Enzymology, 83, 458) can be used.

When the present protein is produced/accumulated as a soluble polypeptide, a culture solution in which a transformant has been cultured as described above is separated into cells or bacterial cells and a medium, for example, by a method such as centrifugation and the like. When the present protein is in a host cell, after collected cells or bacterial cells are washed with a suitable buffer such as a STE solution and the like, cells or bacterial cells are lysed with sonication, a French press, a Manton-Gaulin homogenizer, a Dynomill or the like, and the present protein can be obtained as a cell-free solution by centrifugation or filtration.

A buffer used for separating/purifying the present protein may contain a suitable amount of a surfactant, for example, sodium laurylsulfate (SDS), N-lauroylsarcosine sodium (Sarcosil) or the like.

A method for separating/purifying an objective protein contained in the resulting crude product can be performed by combining the known per se various separating/purifying methods. Examples of these known methods include a solvent extraction method, a salting out method using ammonium sulfate or the like, a dialysis method, a precipitation method using an organic solvent, a ultrafiltration method, a gel filtration, various chromatography methods such as diethylaminoethyl (DEAE)-sepharose chromatography, anion chromatography or ion-exchange chromatography using a resin such as DIAION HPA-75 (Mitsubishi Chemical Corporation) and the like, cation chromatography using lysine such as S-Sepharose FF (Pharmacia) and the like, hydrophobic chromatography using butyl sepharose or the like, and affinity chromatography, various electrophoreses such as SDS-polyacrylamide gel electrophoresis and isoelectric focusing, and the like.

When the present protein is produced/accumulated as an insoluble polypeptide, cells or bacterial cells are separated as described above, and lysed by a suitable method, and a fraction containing the polypeptide is recovered. The recovered sample is solubilized with a solubilizer such as a surfactant such as sodium laurylsulfate (SDS), N-lauroylsarcosine sodium (Sarcosil) and the like. The solubilized solution is diluted or dialyzed to a concentration at which little or no solubilizer is contained, the polypeptide is reconstituted into a normal steric structure, thereafter, a purified specimen can be obtained by a separating/purifying method similar to that described above.

Alternatively, the present protein is produced as a fused protein with other protein, and this can be also purified utilizing affinity chromatography using a substance having affinity for the fused protein (Akio Yamakawa, Experimental Medicine, 13, 469-474 (1995)). Examples of an addition protein to be used in a fused protein include Protein A, FLAG and the like (Proceedings of the National Academy of Sciences USA, 86, 8227 (1989), Genes Development, 4, 1288 (1990), JP-A No. 5-336963, and JP-A No. 6-823021). When Protein A is used, a fused protein of the present protein and Protein A is produced, and this can be purified by performing affinity chromatography using immunoglobulin G. When a FLAG peptide is used, a fused protein of the present protein and FLAG is produced, and this can be purified by affinity chromatography using an anti-FLAG antibody.

The present protein can be produced using an in vitro transcription/translation system according to the known method (Journal of Biomolecular NMR, 6, 129-134 (1995), Science, 242, 1162-1164 (1988), The Journal of Biochemistry, 110, 166-168 (1991)).

The present protein can be chemically synthesized by a chemical synthesis method such as a Fmoc method (fluorenylmethyloxycarbonyl method), a Boc method (t-butyloxycarbonyl method) and the like, or with a commercially available peptide synthesizer, for example, a peptide synthesizer such as APEX396 (Advanced Chemtech), 443A (Applied Biosystems), PS3 (Protein Technologies), 9050 (Perceptive), PSSM-8 (Shimadzu Corporation) and the like.

Structural analysis of the present protein can be performed by a method which is usually used in protein chemistry, for example, the method described in Protein Structural Analysis for Gene Cloning (Hisashi Hirano, published by Tokyo Kagaku Dojin Co., Ltd., 1993). Hydroxylation activity of the present protein can be detected as an amount of production of an N-(5-hydroxy-2-adamantyl)-benzamide derivative by acting the present protein on a compound having an adamantane skeleton, for example, an N-(2-adamantyl)-benzamide derivative which is a substrate. More particularly, a method for culturing a microorganism capable of expressing the present protein in a suitable medium, and detecting an accumulation amount of an N-(5-hydroxy-2-adamantyl)-benzamide derivative accumulated in a medium can be used. Detection of an N-(5-hydroxy-2-adamantyl)-benzamide derivative can be performed, for example, by HPLC using an N-(5-hydroxy-2-adamantyl)-benzamide derivative obtained by the present invention, as a standard product. Specifically, the method described in Example described later can be used.

(vii) Process for Making Variant Polypeptide

Deletion or substitution of an amino acid of the present protein can be performed by a site-directed mutagenesis method which is the technique well-known before filing. Deletion or substitution of one to several amino acids can be prepared according to the methods described in Molecular Cloning: A Laboratory Manual, Second Edition (1989) (Cold Spring Harbor Laboratory Press), Current Protocols in Molecular Biology (1994) (Wiley-Interscience), Nucleic Acids Research, 10 6487 (1982), Proceedings of the National Academy of Sciences USA, 79, 6409 (1982)), Gene 34, 315 (1985), Nucleic Acids Research, 13 4431 (1985), Proceedings of the National Academy of Sciences USA, 82, 488 (1985)), Proceedings of the National Academy of Sciences USA, 81, 5662 (1984)), Science 224, 1431 (1984), WO 85/00817, Nature, 316, 601 (1985) and the like.

(b) Microorganism Capable of Expressing Present Protein

A microorganism which can be used in the present process is not particularly limited as far as it is a microorganism capable of expressing the present protein in the state where it can act with a substrate upon acting with a substrate. Examples include a transformant with the present gene introduced therein and a natural microorganism known to express the present protein such as microorganisms belonging to genus *Bacillus*, preferably *Bacillus subtilis*, genus *Pseudomonas*, genus *Streptomyces* and the like. The microorganism is preferably a transformant in that an amount of the present protein contained in a microorganism can be artificially increased.

A host cell which can be used for making various transformants usable in the present process is not particularly limited as far as it can express the present protein in the state where it can act with a substrate. Examples include the known microorganisms which are usually used such as *Escherichia coli* or *Saccharomyces cerevisiae*, and the known cultured cell such as vertebrate cell (e.g. CHO cell or COS cell) and an insect cell. *Escherichia coli* is preferable in that a proliferation rate is great, and handling is easy. In addition, an expression vector usable for making the transformant is not particularly limited as far as it can express the present protein in the state where it can act with a substrate, and can be arbitrarily selected depending on a kind of a host cell used.

The host cell, the expression vector, the transformant, the method for culturing a transformant and the like are described in detail in the above "(2) Process for producing present protein".

In the present process, when a substrate and a microorganism capable of expressing the present protein are acted, a resting bacterial cell reaction or growing bacterial cell reaction may be used. Each of them can utilize the known method. The resting bacterial cell reaction is a method for culturing a microorganism capable of expressing the present protein, then stopping proliferation of a bacterial cell, and adding a substrate. For example, the method described in Examples 1 to 6 described later can be utilized. The growing bacterial cell reaction is a method for adding a substrate while a microorganism capable of expressing the present protein is cultured.

For example, the method described in Example 7 or 8 described later can be utilized.

In the present process, a reaction condition when a substrate and at least one of:
(a) the present protein or
the present protein and a reducing system consisting of ferredoxin and reductase supplying an electron to the protein, or
(b) a microorganism capable of expressing the present protein are reacted, is preferably as follows.

A reaction temperature can be arbitrarily determined by considering an optimal temperature for the present protein, a temperature for stabilizing a substrate and product, and the like. For example, the reaction can be performed at 10 to 45° C., preferably 15 to 40° C., further preferably 20 to 40° C., and particularly preferably 25 to 35° C.

A reaction pH can be arbitrarily determined by considering an optimal pH for the present protein, pH for stabilizing a substrate and product, and the like. For example, the reaction can be performed at 4 to 10, preferably 5 to 9, further preferably 6 to 9, and particularly preferably 7 to 8.

A reaction time can be arbitrarily determined depending on the above various conditions (i.e. a solvent used, a reaction temperature or a reaction pH), or a kind of a substrate, the present protein or a microorganism used. For example, it is 1 to 100 hours, preferably 5 to 48 hours and more preferably 12 to 36 hours.

An amount of the present protein used is not particularly limited, but the reaction can be performed at a concentration of, for example, 0.5 to 20 µmol/L.

In addition, in the present process, when a substrate and the present protein or a microorganism capable of expressing the present protein are acted, an inclusion agent may be optionally added. Chemical stability or solubility of a substrate in water can be increased, or substrate inhibition on an enzyme or microorganism can be decreased. Examples of the inclusion agent include hydroxypropyl-β-cyclodextrin, α-cyclodextrin, β-cyclodextrin, γ-cyclodextrin, and methyl-β-cyclodextrin (Me-β-CD).

In the present process, when a substrate and the present protein or a microorganism capable of expressing the present protein are acted, a coenzyme (e.g. NADPH or NADH, preferably NADPH) can be optionally coexistent and, further, a regeneration system of the coenzyme can be coexistent. In the present process, by the coexistence of a suitable coenzyme depending on a kind of the present protein used, reactivity thereof can be improved.

In addition, since a coenzyme is consumed with progression of a reaction (e.g. NAD(P)H is consumed, and converted into NAD(P)+), reactivity thereof can be improved by the coexistence of a degeneration system of the coenzyme. As the coenzyme regeneration system, various regeneration systems are known for each coenzyme. Examples of a regeneration system of NAD(P)H include a combination of glucose and glucose dehydrogenase; formic acid and formic acid dehydrogenase; and propanol and alcohol dehydrogenase; and the like.

An addition amount of these coenzymes or the coenzyme regeneration system which can be coexistent in the present process can be arbitrarily determined depending on a kind of a substrate and the present protein or a microorganism used.

A reaction is stopped, and a hydroxylated form of a compound having an adamantane skeleton such as an N-(5-hydroxy-2-adamantyl)-benzamide derivative may be isolated according to a general method for collecting a fermentation product from the reaction product. Specifically, a hydroxylated form of a compound having an adamantane skeleton can be isolated from a medium by solvent extraction, ion-exchange chromatography, active carbon treatment, recrystallization, membrane separation or the like.

The present invention includes an enzyme group utilized for performing the reaction. Examples include the following proteins.

A protein containing an amino acid sequence in which one to several amino acids are deleted, substituted or added in the amino acid sequence of SEQ ID No.: 1, and having hydroxylation activity.

A protein consisting of an amino acid sequence having one to several mutations selected from the group consisting of I77F, L357P, A362T, F41L, I77W, M105I, T234A, F232I, F232L and F232M in the amino acid sequence of SEQ ID No: 1.

A protein consisting of the amino acid sequence of SEQ ID No: 3, or a protein containing an amino acid sequence in which one to several amino acids are deleted, substituted or added in the amino acid sequence, and having hydroxylation activity.

A protein consisting of an amino acid sequence having one to several mutations selected from the group consisting of I77F, I77W, M105I, A196D, F232I, F232L, F232M, T234A, T244A, V399E and K702E in the amino acid sequence of SEQ ID No: 3.

These proteins can be obtained by the method described in the above "Process for producing present protein".

In addition, the present invention includes the following compounds. These compounds are useful for producing an N-(5-hydroxy-2-adamantyl)-benzamide derivative which is a raw material of monohydroxy-2-adamantanamine useful as an intermediate of functional resins or medicines.

A compound of the formula:

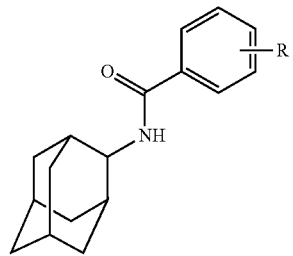

[Formula 13]

a salt or solvate thereof.

In addition, the present invention includes the following compounds. These compounds are useful for producing monohydroxy-2-adamantamine useful as an intermediate of functional resins or medicines.

A compound of the formula:

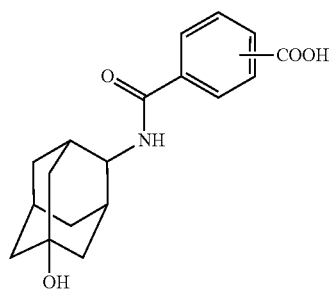

[Formula 14]

a salt or solvate thereof.

Examples of "salt" include salts of inorganic acids such as hydrochloric acid, sulfuric acid, nitric acid, phosphoric acid and the like; salts of organic acids such as paratoluenesulfonic acid, methanesulfonic acid, oxalic acid, citric acid and the like; salts of organic bases such as ammonium, trimethylammonium, triethylammonium and the like; salts of alkali metals such as sodium, potassium and the like; and salts of alkaline earth metals such as calcium, magnesium and the like.

"Solvate" is such that the aforementioned compound may be coordinated with an arbitrarily number of solvent molecules. Preferable is a hydrate.

The present invention will be explained in more detail by way of Examples, but these are not limit the present invention.

As a gene manipulation procedure, unless otherwise indicated, the method described in Molecular Cloning: A Laboratory Manual, Second Edition (Cold Spring Harbor Laboratory) was used.

EXAMPLE 1

Hydroxylation of adamantane by resting bacterial cell reaction using CYP109B1

[Seed Culture]

An expression vector (pET-109B1-CamA-CamB) with a CYP109B1 gene (SEQ ID No: 2) inserted therein was introduced into *Escherichia coli* (BL21(DE3)) to obtain a transformant. The transformant was inoculated in 2 ml of a LB medium, and cultivated at 37° C. on reciprocating shaker at 300 rpm for 24 hours to obtain a seed starter.

[Main Culture]

A M9 mix medium (100 ml) (6.78 g/L $N_{a2}HPO_4$ (anhydrous), 3 g/L $KH_2PO_4$, 0.5 g/L NaCl, 1 g/L $NH_4Cl$, 4 g/L casamino acid, 100 μM $CaCl_2$) was sterilized and, to this were added 100 μl of 100 mM $FeSO_4$ and 1 ml of 2 mg/ml thymine. To this was added Overnight Auto Induction System manufactured by Merck (Solution I 2 ml, Solution II 5 ml, Solution III 100 μl) and, further, 100 μl of 50 mg/ml carbenicillin, and 100 μl of 80 mg/ml 5-aminolevulicic acid were added to obtain a main culture medium. 500 μl of a seed starter was seeded in a 500 ml wide-mouthed Erlenmeyer flask containing 50 ml of a main culture medium, and this was cultured at 25° C. and 120 rpm for 24 hours.

[Biocatalytic Reaction]

The culture solution was centrifuged to remove the supernatant to obtain bacterial cells. The bacterial cells were diluted with 25 ml of a potassium phosphate buffer (50 mM potassium phosphate (pH 7.4), 10% glycerol, 1 mM EDTA, 2 mM DTT, 1 mM D-glucose) so that a bacterial cell concentration in terms of a culture solution became 1-fold, 2.5-fold, and 5-fold, respectively, and placed into a 500 ml Erlenmeyer flask with baffles to obtain a reaction solution. To this reaction solution was added N-(adamantan-2-yl)-phthalamidic acid to a final concentration of 5000 μg/ml, pH 7.4 to initiate a reaction. The reaction was performed at 28° C. and 180 rpm for 31 hours, an equivalent amount of acetone was added, and this was analyzed by reverse-phase HPLC. As a result, a substrate was converted into N-(5-hydroxy-adamantan-2-yl)-phthalamidic acid at a conversion rate described in Table 1.

TABLE 1

| Bacterial cell concentration | 1-fold | 2.5-fold | 5-fold |
| --- | --- | --- | --- |
| Substrate 5000 μg/ml | 61% | 100% | 100% |

EXAMPLE 2

Hydroxylation of adamantane by resting bacterial cell reaction using CYP109FK

[Making of Vector]

Referring to Applied Microbiology and Biotechnology, 2006, vol. 71, p. 455-462, an expression vector of a fused protein (109FK) of CYP109B1 and a P450Rhf reduction domain was prepared. Specifically, for constructing a 109FK gene (SEQ ID No: 4), an Overlap Extension PCR method was used. PCR was performed employing pET-109B1-CamA-CamB as a template, and using a primer 1 (SEQ ID No: 7) and a primer 2 (SEQ ID No: 8), and PCR was performed by employing a genome of genus *Rhodococcus* NCIMB9784 strain as a template, and using a primer 3 (SEQ ID No: 9) and a primer 4 (SEQ ID No: 10). Then, PCR was performed by employing each PCR product as a template, and using primers 1 and 4, and the PCR product was inserted into a cloning vector (pCR-BluntII-TOPO) (pCR-109FK). A fragment containing a 109FK gene was excised with XbaI and BamHI from the pCR-109FK vector, and inserted into an expression vector pET21a to prepare an expression vector of 109FK (pET-109FK).

[Seed Culture]

Into *Escherichia coli* (BL21(DE3)) was introduced pET-109FK, to obtain a transformant. The transformant was seeded into a 96-well deep well plate containing 500 µl of a LB medium per well, and cultured at 900 rpm and 37° C. for 24 hours to obtain a seed starter.

[Main Culture]

Using the main culture medium described in Example 1, the seed starter was inoculated in a 96-well deep well plate containing 500 µl of the main culture medium per well at 5 µl per well, and this was cultured at 25° C. and 900 rpm for 24 hours.

[Biocatalytic Reaction]

A culture solution of the 96-well deep well plate was centrifuged to remove the supernatant, to obtain bacterial cells. The bacterial cells were diluted with 100 µl of a potassium phosphate buffer (50 mM potassium phosphate (pH 7.4), 10% glycerol, 1 mM EDTA, 2 mM DTT, 1 mM D-glucose) containing 1 mg/ml N-(adamantan-2-yl)-phthalamidic acid, to start a reaction. A reaction was performed at 28° C. and 900 rpm for 24 hours. An equivalent amount of acetone was then added, and this was analyzed by reverse-phase HPLC and, as a result, 18% of a substrate was converted into N-(5-hydroxyadamantan-2-yl)-phthalamidic acid.

EXAMPLE 3

Hydroxylation of adamantane by resting bacterial cell reaction using CYP109FK Mutant

[Introduction of Random Mutation]

For introducing a random mutation into a 109FK gene, an Error Prone PCR method was used. Specifically, the Error Prone PCR was performed employing pET-109FK as a template, using primers 1 and 4, and using GeneMorphII Random Mutagenesis Kit manufactured by Stratagene, according to the protocol, so that a mutation frequency became 0 to 4.5/kb. The resulting PCR fragment was restriction enzyme-treated with XbaI and HindIII, and inserted into pET21a to prepare an expression vector (pET-109FKm).

[Screening]

Into *Escherichia coli* (BL21(DE3)) was introduced pET-109FKm, to obtain a transformant. 2296 colonies were collected as the transformant, each colony was inoculated in a 96-well dell well plate containing 500 µl of a LB medium per well, and this was cultured at 900 rpm and 37° C. for 24 hours to obtain a seed starter.

Using the main culture medium described in Example 1, the seed starter was inoculated in a 96-well deep well plate containing 500 µl of the main culture medium per well, at 5 µl per well, and this was cultured at 25° C. and 900 rpm for 24 hours.

A culture solution of the 96-well deep well plate was centrifuged to remove the supernatant, to obtain bacterial cells. The bacterial cells were diluted with 1 ml of a potassium phosphate buffer (50 mM potassium phosphate (pH 7.4), 10% glycerol, 1 mM EDTA, 2 mM DTT, 1 mM D-glucose) containing 1 mg/ml N-(adamantan-2-yl)-phthalamidic acid, to start a reaction. A reaction was performed at 28° C. and 900 rpm for 24 hours. An equivalent amount of acetone was then added, and the resultant was analyzed by reverse-phase HPLC. As a result, 91 colonies had activity which was improved 1.50-fold or more than that of a transformant with pET-109FK introduced therein. A plasmid was extracted from colonies, and a mutation position was identified by sequencing. Regarding I77 and F232 among resulting mutations, substitution with other amino acid was performed by site-directed mutation using QuickChange II Site-Directed Mutagenesis Kit manufactured by Stratagene. Activity of each mutant was confirmed by the same method as that of screening and, as a result, it was found out that mutations described in Table 2 improved activity as compared with other mutations (e.g. mutations described in Table 3).

TABLE 2

|  | Conversion rate | Relative ratio relative to 109FK |
|---|---|---|
| 109FK | 12.9 | 1.00 |
| I77F | 67.8 | 5.26 |
| I77W | 67.8 | 5.27 |
| M105I | 28.0 | 2.17 |
| A196D | 21.2 | 1.64 |
| F232I | 31.7 | 2.47 |
| F232L | 38.7 | 3.01 |
| F232M | 31.7 | 2.46 |
| T234A | 26.3 | 2.04 |
| T244A | 21.8 | 1.70 |
| V399E | 19.0 | 1.48 |
| K702E | 21.9 | 1.70 |

TABLE 3

|  | Conversion rate | Relative ratio relative to 109FK |
|---|---|---|
| M272T | 10.1 | 0.78 |
| F232K | 2.7 | 0.21 |

EXAMPLE 4

Hydroxylation of adamantane by resting bacterial cell reaction using CYP109B1 Mutant by Random Mutation

[Introduction of Random Mutation]

For introducing a random mutation into a CYP109B1 gene, an Error Prone PCR method was used. Specifically, the Error Prone PCR was performed employing pET-109B1-CamA-CamB as a template, using a primer 1 and a primer 5 (SEQ ID No: 11), and using GeneMorphII Random Mutagenesis Kit manufactured by Stratagene, according to the protocol, so that a mutation frequency became 0 to 4.5/kb. The resulting PCR fragment was restriction enzyme-treated with XbaI and KpnI, and inserted into a 7 kb fragment of pET-109B1-

CamA-CamB which had been restriction enzyme-treated with XbaI and KpnI to prepare an expression vector (pET-109B1 m-CamA-CamB).

[Screening]

Into *Escherichia coli* (BL21(DE3)) was introduced pET-109B1m-CamA-CamB, to obtain a transformant. 880 colonies were collected as the transformant, each colony was inoculated in a 96-well deep well plate containing 500 μl of a LB medium per well, and this was cultured at 900 rpm and 37° C. for 24 hours to obtain a seed starter.

Using the main culture medium described in Example 1, the seed starter was inoculated in a 96-well deep well plate containing 500 μl of the main culture medium per well, at 5 μl per well, and this was cultured at 25° C. and 900 rpm for 24 hours.

A culture solution of the 96-well deep well plate was centrifuged to remove the supernatant to obtain bacterial cells. The bacterial cells were diluted with 500 μl of a potassium phosphate buffer (50 mM potassium phosphate (pH 7.4), 10% glycerol, 1 mM EDTA, 2 mM DTT, 1 mM D-glucose) containing 1 mg/ml N-(adamantan-2-yl)-phthalamidic acid, to start a reaction. A reaction was performed at 28° C. and 900 rpm for 2 hours. An equivalent amount of acetone was then added, the resultant was analyzed by reverse-phase HPLC. As a result, 16 colonies had activity which was improved 1.23-fold or more than that of a transformant with pET-109FK introduced therein. A plasmid was extracted from colonies, and a mutation position was identified by sequencing. Activity of each mutation was reconfirmed by the same method as that of screening and, as a result, it was found out that mutations described in Table 4 improved activity as compared with other mutations (e.g. mutations described in Table 5).

TABLE 4

|       | Conversion rate | Relative ratio relative to 109B1 |
|-------|-----------------|----------------------------------|
| 109B1 | 23.2            | 1.00                             |
| I77F  | 33.5            | 1.44                             |
| L357P | 30.3            | 1.31                             |
| A362T | 27.1            | 1.17                             |
| F41L  | 26.7            | 1.15                             |

TABLE 5

|       | Conversion rate | Relative ratio relative to 109B1 |
|-------|-----------------|----------------------------------|
| E242K | 14.3            | 0.62                             |
| Q46R  | 23.2            | 1.00                             |

EXAMPLE 5

Hydroxylation of adamantane by resting bacterial cell reaction using CYP109B1 Mutant with Mutation of CYP109FK Mutant Introduced Therein A part of mutation of the 109FK gene found out in Example 3 was introduced into a CYP109B1 gene, and activity was measured by the method for screening of Example 4. In this respect, bacterial cells were diluted with 1 ml of a potassium phosphate buffer (50 mM potassium phosphate (pH 7.4), 10% glycerol, 1 mM EDTA, 2 mM DTT, 1 mM D-glucose) containing 3 mg/ml N-(adamantan-2-yl)-phthalamidic acid, and a reaction time was changed to 16 hours. As a result, it was found out that mutations described in Table 6 improved activity.

TABLE 6

|       | Conversion rate | Relative ratio relative to 109B1 |
|-------|-----------------|----------------------------------|
| 109B1 | 47.9            | 1.00                             |
| I77F  | 70.9            | 1.48                             |
| I77W  | 61.2            | 1.28                             |
| M105I | 57.5            | 1.20                             |
| T234A | 55.8            | 1.17                             |

On the other hand, confirmation of activity of the CYP109B1 gene in which mutation was introduced into F232 was performed by the method for screening of Example 4. As a result, it was found out that mutations described in Table 7 improved activity.

TABLE 7

|       | Conversion rate | Relative ratio relative to 109B1FK |
|-------|-----------------|------------------------------------|
| 109B1 | 9.6             | 1.00                               |
| F232I | 14.9            | 1.55                               |
| F232L | 14.8            | 1.55                               |
| F232M | 15.7            | 1.64                               |

EXAMPLE 6

Hydroxylation of adamantane by resting bacterial cell reaction using CYP109B1 Mutant (I77F)

[Seed Culture]

An expression vector (pET-109B1 (I77F)-CamA-CamB) with a CYP109B1 mutant (I77F) gene (SEQ ID No: 5) inserted therein was introduced into *Escherichia coli* (BL21 (DE3)) to obtain a transformant. The transformant was inoculated in 2 ml of LB medium, and cultured with a 300 rpm reciprocating shaker at 37° C. for 24 hours to obtain a seed starter.

[Main Culture]

Main culture was performed as in Example 1.

[Biocatalytic Reaction]

A Biocatalytic reaction was performed as in Example 1. After the reaction, an equivalent amount of acetone was added, the resultant was analyzed by reverse-phase HPLC and, as a result, a substrate was converted into N-(5-hydroxy-adamantan-2-yl)-phthalamidic acid at a conversion rate in Table 8.

TABLE 8

| Bacterial cell concentration | 1-fold | 2.5-fold | 5-fold |
|------------------------------|--------|----------|--------|
| Substrate 5000 μg/ml         | 88%    | 100%     | 100%   |

[Purification]

After the reaction solution as a whole was centrifuged, 113 ml of the supernatant was obtained. The supernatant (40 ml) was adsorbed onto 5 ml of HP20SS, and this was 2CV-washed with a 0.1% aqueous formic acid solution, and eluted with 0.1% formic acid, and a 50% aqueous acetone solution to obtain an active fraction. The active fraction was concentrated, and lyophilized to obtain 125 mg of a powder of N-(5-hydroxy-adamantan-2-yl)-phthalamidic acid. A structure was analyzed by NMR and, as a result, since NOE was observed between H of 3.92, and H of 1.71 and 1.62, it was found out that the structure was Anti entity 100%. 1H NMR (DMSO-d6) δ : 8.40 (1H, br. s), 7.74 (1H, br. s), 7.522 (1H, td, J=7.5, 1.1 Hz), 7.461 (1H, td, J=7.5, 1.1 Hz), 7.40 (1H, br. d, J=~8 Hz), 4.40 (1H, br. s), 3.92 (1H, m), 2.05 (2H, br. s), 1.97

(2H, m), 1.96 (1H, m), 1.71 (2H, br. d), 1.62 (2H, br. d, J=~12 Hz), 1.61 (1H, br. s), 1.28 (2H, br. d, J=~12 Hz)

EXAMPLE 7

Hydroxylation of adamantane by growing bacterial cell reaction using CYP109B1 Mutant (I77F)
[Seed Culture]
A expression vector (pET-109B1 (I77F)-CamA-CamB) with a CYP109B1 mutant (I77F) gene (SWQ ID No: 5) inserted therein was introduced into *Escherichia coli* (BL21 (DE3)) to obtain a transformant.
One platinum loop of the transformant was seeded in a 500 ml wide-mouthed Erlenmeyer flask containing 50 ml of LB medium, and cultured at 37° C. and 180 rpm for 5.5 hours to obtain a seed starter.
[Main Culture]
1 L of a L medium (10 g/L triptone, 5 g/L yeast extract, 5 g/L NaCl) was sterilized, to this were added 1 ml of 100 mM FeSO$_4$, 20 g of glycerol, 30 g of hydroxypropyl-β-cyclodextrin, 10 ml of 50 mg/ml carbenicillin, 10 ml of 80 mg/ml 5-aminolevulicic acid, 10 ml of 2 mg/ml thymine, 0.1 g of MgCl$_2$, and 0.1 ml of Adecanol LG121, and N-(adamantan-2-yl)-phthalamidic acid which is a substrate was added to a final concentration of 5000 µg/ml, to obtain a main culture medium. A seed starter (40 ml) was seeded in 3 L-minijar containing 1 L of the main culture medium, and culturing was initiated by controlling at 28° C., 600 rpm and pH 6.5. Six hours after culturing initiation, IPTG was added to a final concentration of 1 mM. During culturing, casamino acid, glycerol, and a substrate were arbitrarily added, and an amount of a finally added substrate reached 30 g/L. Seventy-two hours after reaction initiation, the reaction was analyzed by reverse-phase HPLC and, as a result, 67% of the substrate was converted into N-(5-hydroxy-adamantan-2-yl)-phthalamidic acid.

EXAMPLE 8

Hydroxylation of adamantane by growing bacterial cell reaction using CYP109B1 Mutant (I77F) and Production of Monohydroxy-2-Adamantanamine
[Production of Vector]
An *Escherichia coli* JM109 strain-derived glycerol dehydrogenase gene (SEQ ID No: 6) was inserted into pCDFDuet to construct an expression vector (pCDFD-GLD).
[Seed Culture]
Into *Escherichia coli* (BL21(DE 3)) were introduced pCDFD-GLD, and pET-109B1 (I77F)-CamA-CamB described in Example 7, to obtain a transformant. One platinum loop of the transformant was seeded in a 500 ml wide-mouthed Erlenmeyer flask containing 50 ml of LB medium, and cultured at 37° C. and 180 rpm for 7 hours to obtain a seed starter.
[Main Culture]
1 L of a L medium/M9 (10 g/L triptone, 5 g/L yeast extract, 6.78 g/L Na$_2$HPO$_4$ (anhydrous), 3 g/L KH$_2$PO$_4$, 5.5 g/L NaCl, 1 g/L NH$_4$Cl) was sterilized, to this were added 1 ml of 100 mM FeSO$_4$, 20 g of glycerol, 30 g of hydroxypropyl-β-cyclodextrin, 1 ml of 50 mg/ml carbenicillin, 1 ml of 50 mg/ml streptomycin, 1 ml of 80 mg/ml 5-aminolevric acid, and 10 ml of 2 mg/ml thymine. Further, Overnight Auto Induction System manufactured by Merck (Solution I 20 ml, Solution II 50 ml, Solution III 1 ml) was added, and N-(adamantan-2-yl)-phthalamidic acid which is a substrate was added to a final concentration of 5000 µg/ml, to obtain a main culture medium. A seed starter (40 ml) was seeded in 3 L-minijar containing 1 L of the main culture medium, and culturing was initiated by controlling at 28° C., 500 rpm, and pH 6.5. During culturing, casamino acid, glycerol, and a substrate were arbitrarily added, and an amount of a finally added substrate reached 30 g/L. Seventy-two hours after reaction initiation, the reaction was analyzed by reverse-phase HPLC and, as a result, 90% of the substrate was converted into N-(5-hydroxy-adamantan-2-yl)-phthalamidic acid.
[Purification]
A culture solution was adjusted with hydrochloric acid to pH of 4, and sterilized at 120° C. for 15 minutes, and a protecting group was deprotected. A pH was adjusted with an aqueous sodium hydroxide solution to 7, and the resultant was centrifuged to obtain 1.65 L of the supernatant. 1 L of the supernatant was adsorbed on 300 ml of an ammonium ion-type Diaion PK208, and this was eluted with 2 N aqueous ammonia to obtain an active fraction. The active fraction was concentrated, lyophilized, dissolved in 100 ml of water, and adsorbed onto 120 ml of hydroxide ion-type Amberlite IRA410. This was eluted with water, and an active fraction was obtained, concentrated, and lyophilized to obtain 9.64 g of a powder of monohydroxy-2-adamantamine. A purity was measured by the FDLA method and, as a result, a purity of monohydroxy-2-adamantamine was 96.6%.

EXAMPLE 9

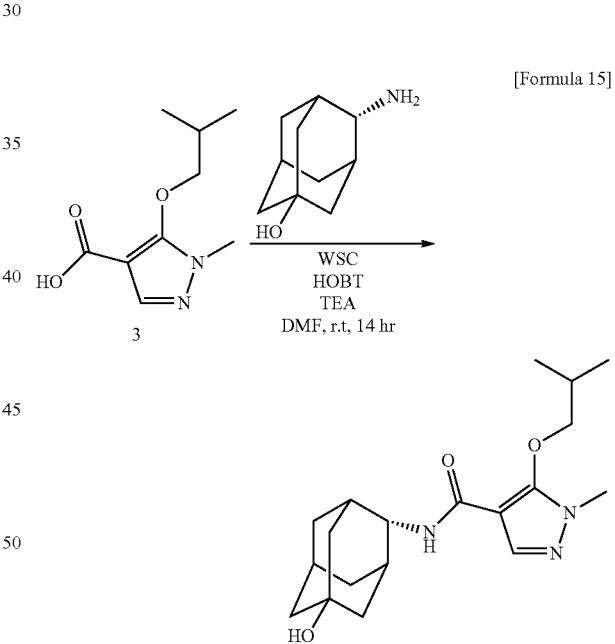

[Formula 15]

To a solution of Compound 3 (150 mg) in dimethylformamide (DMF) (5 ml) were added monohydroxy-2-adamantanamine (140 mg), 1-hydroxybenzotriazole (HOBT) (31 mg), 1-(3-dimethylaminopropyl)-3-ethylcarbodiimide hydrochloride (WSC) (174 mg), and triethylamine (TEA) (180 ml) under the nitrogen atmosphere, and the mixture was stirred at room temperature for 14 hours. After completion of the reaction, 2N hydrochloric acid (30 ml) was added, followed by extraction with ethyl acetate. The organic layer was sequentially washed with an aqueous saturated sodium bicarbonate solution and an aqueous saturated sodium chloride solution, and dried over magnesium sulfate. A solvent was removed, and the residue was purified by silica gel chromatography to obtain Compound 4 (226 mg).

NMR: (CDCl$_3$); 1.06 (d, J=6.6 Hz, 6H), 1.53-2.20 (m, 14H), 3.72 (s, 3H), 3.98 (d, J=6.6 Hz, 2H), 6.25-6.30 (m, 1H), 7.71 (s, 1H)

Industrial Applicability

The present process can be utilized as a process for producing a hydroxylated form of a compound having an adamantane skeleton useful as an intermediate for functional resins and medicines, at low cost and with high yield.

Sequence Listing Free Text

SEQ ID No: 1 represents an amino acid sequence of CYP109B1.

SEQ ID No: 2 represents a base sequence of a gene encoding CYP109B1 used in Example 1.

SEQ ID No: 3 represents an amino acid sequence of CYP109FK.

SEQ ID No: 4 represents a base sequence of a gene encoding CYP109FK.

SEQ ID No: 5 represents a base sequence of a gene encoding a CYP109B1 mutant (I77F).

SEQ ID No: 6 represents a glycerol dehydrogenase gene derived from *Escherichia coli* JM109 strain.

The invention claimed is:

1. A protein comprising the amino acid sequence of SEQ ID NO: 1 and having from 1 to 5 mutations, at least one of said mutations being a substitution mutation at amino acid 77 of SEQ ID NO: 1, and which has hydroxylating activity.

2. The protein of claim 1 in which the substitution mutation at amino acid 77 is to phenylalanine or tryptophan.

3. The protein of claim 1 in which a second mutation is selected from the group consisting of L357P, A362T, F41L, M105I, T234A, F232I, F232L and F232M.

4. The protein of claim 2 in which a second mutation is selected from the group consisting of L357P, A362T, F41L, M105I, T234A, F232I, F232L and F232M.

5. The protein of claim 1 that has activity of hydroxylating a compound having an adamantane skeleton.

6. The protein of claim 2 that has activity of hydroxylating a compound having an adamantane skeleton.

7. The protein of claim 3 that has activity of hydroxylating a compound having an adamantane skeleton.

8. The protein of claim 4 that has activity of hydroxylating a compound having an adamantane skeleton.

9. The protein of claim 1 that has activity of hydoxylating N-(adarnantan-2-yl)-phthalamidie acid that is at least 1.4x the activity of wild-type CYP109B1 enzyme.

* * * * *

SEQUENCE LISTING

```
<160> NUMBER OF SEQ ID NOS: 11

<210> SEQ ID NO 1
<211> LENGTH: 396
<212> TYPE: PRT
<213> ORGANISM: Bacillus subtilis
<220> FEATURE:
<222> LOCATION: (2)..(2)
<223> OTHER INFORMATION: Xaa is Asp or Asn residue.
<220> FEATURE:
<222> LOCATION: (113)..(113)
<223> OTHER INFORMATION: Xaa is Arg or Gln residue.

<400> SEQUENCE: 1
```

Met Xaa Val Leu Asn Arg Arg Gln Ala Leu Gln Arg Ala Leu Leu Asn
1               5                   10                  15

Gly Lys Asn Lys Gln Asp Ala Tyr His Pro Phe Pro Trp Tyr Glu Ser
            20                  25                  30

Met Arg Lys Asp Ala Pro Val Ser Phe Asp Glu Glu Asn Gln Val Trp
        35                  40                  45

Ser Val Phe Leu Tyr Asp Asp Val Lys Val Val Gly Asp Lys Glu
    50                  55                  60

Leu Phe Ser Ser Cys Met Pro Gln Gln Thr Ser Ser Ile Gly Asn Ser
65                  70                  75                  80

Ile Ile Asn Met Asp Pro Pro Lys His Thr Lys Ile Arg Ser Val Val
                85                  90                  95

Asn Lys Ala Phe Thr Pro Arg Val Met Lys Gln Trp Glu Pro Arg Ile
            100                 105                 110

Xaa Glu Ile Thr Asp Glu Leu Ile Gln Lys Phe Gln Gly Arg Ser Glu
        115                 120                 125

Phe Asp Leu Val His Asp Phe Ser Tyr Pro Leu Pro Val Ile Val Ile
    130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Leu Ala
            180                 185                 190

Ala Phe Phe Ala Gly Ile Ile Glu Glu Lys Arg Asn Lys Pro Glu Gln
        195                 200                 205

Asp Ile Ile Ser Ile Leu Val Glu Ala Glu Glu Thr Gly Glu Lys Leu
    210                 215                 220

Ser Gly Glu Glu Leu Ile Pro Phe Cys Thr Leu Leu Leu Val Ala Gly
225                 230                 235                 240

```
Asn Glu Thr Thr Thr Asn Leu Ile Ser Asn Ala Met Tyr Ser Ile Leu
                245                 250                 255

Glu Thr Pro Gly Val Tyr Glu Glu Leu Arg Ser His Pro Glu Leu Met
            260                 265                 270

Pro Gln Ala Val Glu Glu Ala Leu Arg Phe Arg Ala Pro Ala Pro Val
        275                 280                 285

Leu Arg Arg Ile Ala Lys Arg Asp Thr Glu Ile Gly Gly His Leu Ile
    290                 295                 300

Lys Gly Asp Met Val Leu Ala Phe Val Ala Ser Ala Asn Arg Asp
305                 310                 315                 320

Glu Ala Lys Phe Asp Arg Pro His Met Phe Asp Ile Arg His Pro
                325                 330                 335

Asn Pro His Ile Ala Phe Gly His Gly Ile His Phe Cys Leu Gly Ala
                340                 345                 350

Pro Leu Ala Arg Leu Glu Ala Asn Ile Ala Leu Thr Ser Leu Ile Ser
            355                 360                 365

Ala Phe Pro His Met Glu Cys Val Ser Ile Thr Pro Ile Glu Asn Ser
        370                 375                 380

Val Ile Tyr Gly Leu Lys Ser Phe Arg Val Lys Met
385                 390                 395
```

<210> SEQ ID NO 2
<211> LENGTH: 1191
<212> TYPE: DNA
<213> ORGANISM: Bacillus subtilis

<400> SEQUENCE: 2

```
atggatgtgt taaaccgccg gcaagccttg cagcgagcgc tgctcaatgg gaaaaacaaa        60
caggatgcgt atcatccgtt tccatggtat gaatcgatga gaaggatgc gcctgtttcc       120
tttgatgaag aaaaccaagt gtggagcgtt tttctttatg atgatgtcaa aaaagttgtt       180
ggggataaag agttgttttc cagttgcatg ccgcagcaga caagctctat tggaaattcc       240
atcattaaca tggaccccgcc gaagcataca aaaatccgtt cagtcgtgaa caaagccttt       300
actccgcgcg tgatgaagca atgggaaccg agaattcgag aaatcacaga tgaactgatt       360
caaaaatttc aggggcgcag tgagtttgac cttgttcacg attttcata cccgcttccg       420
gttattgtga tatctgagtt gctgggagtg ccttcagcgc atatggaaca gtttaaagca       480
tggtctgatc ttctggtcag tacaccgaag gataaaagtg aagaagctga aaaagccttt       540
ttggaagaac gagataagtg tgaggaagaa ctggccgcgt ttttgccgg catcatagaa       600
gaaaagcgaa acaaaccgga acaggatatt atttctattt tagtggaagc ggaagaaaca       660
ggcgagaagc tgtccggtga agagctgatt ccgttttgca cgctgctgct ggtgccggaa       720
aatgaaacca ctacaaacct gatttcaaat gcgatgtaca gcatattaga aacgccaggc       780
gtttacgagg aactgcgcag ccatcctgaa ctgatgcctc aggcagtgga ggaagccttg       840
cgtttcagag cgccggcccc ggtttttgagg cgcattgcca agcgggatac ggagatcggg       900
gggcacctga ttaaagaagg tgatatggtt ttggcgtttg tggcatcggc aaatcgtgat       960
gaagcaaagt ttgacagacc gcacatgttt gatatccgcc gccatccaa tccgcatatt      1020
gcgtttggcc acggcatcca ttttgcctt ggggccccgc ttgcccgtct tgaagcaaat      1080
atcgcgttaa cgtcttttgat ttctgctttt cctcatatgg agtgcgtcag tatcactccg      1140
attgaaaaca gtgtgatata cggattaaag agcttccgtg tgaaaatgta a             1191
```

<210> SEQ ID NO 3

```
<211> LENGTH: 727
<212> TYPE: PRT
<213> ORGANISM: Artificial sequence
<220> FEATURE:
<223> OTHER INFORMATION: A protein containing fused CYP109B1 and and
      P450Rhf reductase domain

<400> SEQUENCE: 3
```

| | | | | | | | | | | | | | | |
|---|---|---|---|---|---|---|---|---|---|---|---|---|---|---|
|Met|Asp|Val|Leu|Asn|Arg|Arg|Gln|Ala|Leu|Gln|Arg|Ala|Leu|Leu|Asn|
|1| | | |5| | | | |10| | | | |15|

Gly Lys Asn Lys Gln Asp Ala Tyr His Pro Phe Pro Trp Tyr Glu Ser
           20                  25                  30

Met Arg Lys Asp Ala Pro Val Ser Phe Asp Glu Glu Asn Gln Val Trp
       35                  40                  45

Ser Val Phe Leu Tyr Asp Asp Val Lys Val Val Gly Asp Lys Glu
 50                  55                  60

Leu Phe Ser Ser Cys Met Pro Gln Gln Thr Ser Ser Ile Gly Asn Ser
 65                  70                  75                  80

Ile Ile Asn Met Asp Pro Pro Lys His Thr Lys Ile Arg Ser Val Val
                 85                  90                  95

Asn Lys Ala Phe Thr Pro Arg Val Met Lys Gln Trp Glu Pro Arg Ile
             100                 105                 110

Arg Glu Ile Thr Asp Glu Leu Ile Gln Lys Phe Gln Gly Arg Ser Glu
         115                 120                 125

Phe Asp Leu Val His Asp Phe Ser Tyr Pro Leu Pro Val Ile Val Ile
130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Glu Leu Ala
            180                 185                 190

Ala Phe Phe Ala Gly Ile Ile Glu Glu Lys Arg Asn Lys Pro Glu Gln
        195                 200                 205

Asp Ile Ile Ser Ile Leu Val Glu Ala Glu Thr Gly Glu Lys Leu
210                 215                 220

Ser Gly Glu Glu Leu Ile Pro Phe Cys Thr Leu Leu Leu Val Ala Gly
225                 230                 235                 240

Asn Glu Thr Thr Thr Asn Leu Ile Ser Asn Ala Met Tyr Ser Ile Leu
                245                 250                 255

Glu Thr Pro Gly Val Tyr Glu Glu Leu Arg Ser His Pro Glu Leu Met
            260                 265                 270

Pro Gln Ala Val Glu Glu Ala Leu Arg Phe Arg Ala Pro Ala Pro Val
        275                 280                 285

Leu Arg Arg Ile Ala Lys Arg Asp Thr Glu Ile Gly Gly His Leu Ile
290                 295                 300

Lys Glu Gly Asp Met Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Gly His Gly Ile His Phe Cys Leu Gly Ala
            340                 345                 350

Pro Leu Ala Arg Leu Glu Ala Asn Ile Ala Leu Thr Ser Leu Ile Ser
        355                 360                 365

Ala Phe Pro His Met Glu Cys Val Ser Ile Thr Pro Ile Glu Asn Ser
370                 375                 380

```
Val Ile Tyr Gly Leu Lys Ser Phe Arg Val Lys Met Glu Phe Val Leu
385                 390                 395                 400

His Arg His Gln Pro Val Thr Ile Gly Glu Pro Ala Ala Arg Ala Val
            405                 410                 415

Ser Arg Thr Val Thr Val Glu Arg Leu Asp Arg Ile Ala Asp Asp Val
        420                 425                 430

Leu Arg Leu Val Leu Arg Asp Ala Gly Gly Lys Thr Leu Pro Thr Trp
    435                 440                 445

Thr Pro Gly Ala His Ile Asp Leu Asp Leu Gly Ala Leu Ser Arg Gln
450                 455                 460

Tyr Ser Leu Cys Gly Ala Pro Asp Ala Pro Ser Tyr Glu Ile Ala Val
465                 470                 475                 480

His Leu Asp Pro Glu Ser Arg Gly Gly Ser Arg Tyr Ile His Glu Gln
            485                 490                 495

Leu Glu Val Gly Ser Pro Leu Arg Met Arg Gly Pro Arg Asn His Phe
        500                 505                 510

Ala Leu Asp Pro Gly Ala Glu His Tyr Val Phe Val Ala Gly Gly Ile
    515                 520                 525

Gly Ile Thr Pro Val Leu Ala Met Ala Asp His Ala Arg Ala Arg Gly
530                 535                 540

Trp Ser Tyr Glu Leu His Tyr Cys Gly Arg Asn Arg Ser Gly Met Ala
545                 550                 555                 560

Tyr Leu Glu Arg Val Ala Gly His Gly Asp Arg Ala Ala Leu His Val
            565                 570                 575

Ser Glu Glu Gly Thr Arg Ile Asp Leu Ala Ala Leu Leu Ala Glu Pro
        580                 585                 590

Ala Pro Gly Val Gln Ile Tyr Ala Cys Gly Pro Gly Arg Leu Leu Ala
    595                 600                 605

Gly Leu Glu Asp Ala Ser Arg Asn Trp Pro Asp Gly Ala Leu His Val
610                 615                 620

Glu His Phe Thr Ser Ser Leu Ala Ala Leu Asp Pro Asp Val Glu His
625                 630                 635                 640

Ala Phe Asp Leu Glu Leu Arg Asp Ser Gly Leu Thr Val Arg Val Glu
            645                 650                 655

Pro Thr Gln Thr Val Leu Asp Ala Leu Arg Ala Asn Asn Ile Asp Val
        660                 665                 670

Pro Ser Asp Cys Glu Glu Gly Leu Cys Gly Ser Cys Glu Val Ala Val
    675                 680                 685

Leu Asp Gly Glu Val Asp His Arg Asp Thr Val Leu Thr Lys Ala Glu
690                 695                 700

Arg Ala Ala Asn Arg Gln Met Met Thr Cys Cys Ser Arg Ala Cys Gly
705                 710                 715                 720

Asp Arg Leu Ala Leu Arg Leu
            725
```

<210> SEQ ID NO 4
<211> LENGTH: 2184
<212> TYPE: DNA
<213> ORGANISM: Artificial sequence
<220> FEATURE:
<223> OTHER INFORMATION: A gene coding a protein containing fused
    CYP109B1 and P450Rhf reductase domain

<400> SEQUENCE: 4
atggatgtgt taaaccgccg gcaagccttg cagcgagcgc tgctcaatgg gaaaaacaaa    60

| | |
|---|---|
| caggatgcgt atcatccgtt tccatggtat gaatcgatga gaaaggatgc gcctgtttcc | 120 |
| tttgatgaag aaaaccaagt gtggagcgtt tttctttatg atgatgtcaa aaaagttgtt | 180 |
| ggggataaag agttgttttc cagttgcatg ccgcagcaga caagctctat tggaaattcc | 240 |
| atcattaaca tggaccccgcc gaagcataca aaaatccgtt cagtcgtgaa caaagccttt | 300 |
| actccgcgcg tgatgaagca atgggaaccg agaattcgag aaatcacaga tgaactgatt | 360 |
| caaaaatttc aggggcgcag tgagtttgac cttgttcacg attttcata cccgcttccg | 420 |
| gttattgtga tatctgagtt gctgggagtg ccttcagcgc atatggaaca gtttaaagca | 480 |
| tggtctgatc ttctggtcag tacaccgaag ataaaagtg aagaagctga aaagcctttt | 540 |
| ttggaagaac gagataagtg tgaggaagaa ctggccgcgt ttttgccgg catcatagaa | 600 |
| gaaaagcgaa acaaaccgga acaggatatt atttctattt tagtggaagc ggaagaaaca | 660 |
| ggcgagaagc tgtccggtga agagctgatt ccgttttgca cgctgctgct ggtggccgga | 720 |
| aatgaaacca ctacaaacct gatttcaaat gcgatgtaca gcatattaga aacgccaggc | 780 |
| gtttacgagg aactgcgcag ccatcctgaa ctgatgcctc aggcagtgga ggaagccttg | 840 |
| cgtttcagag cgccggcccc ggttttgagg cgcattgcca agcgggatac ggagatcggg | 900 |
| gggcacctga ttaaagaagg tgatatggtt ttggcgtttg tggcatcggc aaatcgtgat | 960 |
| gaagcaaagt ttgacagacc gcacatgttt gatatccgcc gccatcccaa tccgcatatt | 1020 |
| gcgtttggcc acggcatcca ttttgccttt ggggccccgc ttgcccgtct tgaagcaaat | 1080 |
| atcgcgttaa cgtctttgat ttctgctttt cctcatatgg agtgcgtcag tatcactccg | 1140 |
| attgaaaaca gtgtgatata cggattaaag agcttccgtg tgaaaatgga attcgtgctg | 1200 |
| caccgccatc aaccggtcac catcggagaa cccgccgccc gggcggtgtc ccgcaccgtc | 1260 |
| accgtcgagc gcctggaccg gatcgccgac gacgtgctgc cctcgtcct gcgcgacgcc | 1320 |
| ggcgaaaga cattgcccac gtggactccc ggcgcccata tcgacctcga cctcggcgcg | 1380 |
| ctgtcgcgcc agtactccct gtgcggcgcg cccgatgcgc cgagctacga gattgccgtg | 1440 |
| cacctggatc ccgagagccg cggcggttcg cgctacatcc acgaacagct cgaggtggga | 1500 |
| agcccgctcc ggatgcgcgg ccctcggaac catttcgcgc tcgaccccgg cgccgagcac | 1560 |
| tacgtgttcg tcgccggcgg catcggcatc accccagtcc tggccatggc cgaccacgcc | 1620 |
| cgcgcccggg ggtggagcta cgaactgcac tactgcggcc gaaaccgttc cggcatggcc | 1680 |
| tatctcgagc gtgtcgccgg gcacggtgac cgggccgccc tgcacgtgtc cgaggaaggc | 1740 |
| acccggatcg acctcgccgc cctcctcgcc gagcccgccc ccggcgtcca gatctacgcg | 1800 |
| tgcgggcccg gcggctgctc gccggactc gaggacgcga gccggaactg gcccgacggg | 1860 |
| gcgctgcacg tcgagcactt cacctcgtcc ctcgcggcgc tcgatccgga cgtcgagcac | 1920 |
| gccttcgacc tcgaactgcg tgactcgggg ctgaccgtgc gggtcgaacc cacccagacc | 1980 |
| gtcctcgacg cgttgcgcgc caacaacatc gacgtgccca cgcactgcga ggaaggcctc | 2040 |
| tgcggctcgt gcgaggtcgc cgtcctcgac ggcgaggtcg accatcgcga cacggtgctg | 2100 |
| accaaggccg agcgggcggc gaaccggcag atgatgacct gctgctcgcg tgcctgtggc | 2160 |
| gaccggctgg ccctgcgact ctga | 2184 |

<210> SEQ ID NO 5
<211> LENGTH: 1191
<212> TYPE: DNA
<213> ORGANISM: Artificial sequence
<220> FEATURE:
<223> OTHER INFORMATION: A gene coding a protein CYP109B1 with I77F
      mutation

<400> SEQUENCE: 5

```
atggatgtgt taaaccgccg gcaagccttg cagcgagcgc tgctcaatgg gaaaaacaaa      60
caggatgcgt atcatccgtt tccatggtat gaatcgatga aaaggatgc gcctgtttcc      120
tttgatgaag aaaaccaagt gtggagcgtt tttctttatg atgatgtcaa aaaagttgtt      180
ggggataaag agttgttttc cagttgcatg ccgcagcaga caagctcttt tggaaattcc      240
atcattaaca tggacccgcc gaagcataca aaaatccgtt cagtcgtgaa caaagccttt      300
actccgcgcg tgatgaagca atgggaaccg agaattcgag aaatcacaga tgaactgatt      360
caaaaatttc aggggcgcag tgagtttgac cttgttcacg attttcata cccgcttccg      420
gttattgtga tatctgagtt gctgggagtg ccttcagcgc atatgaaca gtttaaagca      480
tggtctgatc ttctggtcag tacaccgaag gataaaagtg aagaagctga aaaagccttt      540
ttggaagaac gagataagtg tgaggaagaa ctggccgcgt tttttgccgg catcatagaa      600
gaaaagcgaa acaaaccgga acaggatatt atttctattt tagtggaagc ggaagaaaca      660
ggcgagaagc tgtccggtga agagctgatt ccgttttgca cgctgctgct ggtggccgga      720
aatgaaacca ctacaaacct gatttcaaat gcgatgtaca gcatattaga aacgccaggc      780
gtttacgagg aactgcgcag ccatcctgaa ctgatgcctc aggcagtgga ggaagccttg      840
cgtttcagag cgccggcccc ggttttgagg cgcattgcca gcgggatac ggagatcggg      900
gggcacctga ttaaagaagg tgatatggtt ttggcgtttg tggcatcggc aaatcgtgat      960
gaagcaaagt tgacagacc gcacatgttt gatatccgcc gccatcccaa tccgcatatt      1020
gcgtttggcc acggcatcca tttttgcctt ggggccccgc ttgcccgtct gaagcaaat      1080
atcgcgttaa cgtctttgat ttctgctttt cctcatatgg agtgcgtcag tatcactccg      1140
attgaaaaca gtgtgatata cggattaaag agcttccgtg tgaaaatgta a             1191
```

<210> SEQ ID NO 6
<211> LENGTH: 1104
<212> TYPE: DNA
<213> ORGANISM: Escherichia coli

<400> SEQUENCE: 6

```
atggaccgca ttattcaatc accgggtaaa tacatccagg gcgctgatgt gattaatcgt      60
ctgggcgaat acctgaagcc gctggcagaa cgctggttag tggtgggtga caaatttgtt      120
ttaggttttg ctcaatccac tgtcgagaaa gctttaaag atgctggact ggtagtagaa      180
attgcgccgt ttggcggtga atgttcgcaa aatgagatcg accgtctgcg tggcatcgcg      240
gagactgcgc agtgtggcgc aattctcggt atcggtggcg aaaaaccct cgatactgcc      300
aaagcactgg cacatttcat gggtgttccg gtagcgatcc accgactat cgcctctacc      360
gatgcaccgt gcagcgcatt gtctgttatc tacaccgatg agggtgagtt tgaccgctat      420
ctgctgttgc aaataaccc gaatatgtc attgtcgaca ccaaaatcgt cgctggcgca      480
cctgcacgtc tgttagcggc gggtatcggc gatgcgctgg caacctggtt tgaagcgcgt      540
gcctgctctc gtagcggcgc gaccaccatg gcgggcggca agtgcaccca ggctgcgctg      600
gcactggctg aactgtgcta aacacccctg ctggaagaag gcgaaaaagc gatgcttgct      660
gccgaacagc atgtagtgac tccggcgctg agcgcgtga ttgaagcgaa cacctatttg      720
agcggtgttg gttttgaaag tggtggtctg gctgcggcgc acgcagtgca taacggcctg      780
accgctatcc cggacgcgca tcactattat cacggtgaaa aagtggcatt cggtacgctg      840
acgcagctgg ttctggaaaa tgcgccggtg gaggaaatcg aaaccgtagc tgcccttagc      900
```

```
catgcggtag gtttgccaat aactctcgct caactggata ttaaagaaga tgtcccggcg      960
aaaatgcgaa ttgtggcaga agcggcatgt gcagaaggtg aaaccattca acacatgcct     1020
ggcggcgcga cgccagatca ggtttacgcc gctctgctgg tagccgacca gtacggtcag     1080
cgtttcctgc aagagtggga ataa                                            1104

<210> SEQ ID NO 7
<211> LENGTH: 29
<212> TYPE: DNA
<213> ORGANISM: Artificial sequence
<220> FEATURE:
<223> OTHER INFORMATION: Primer 1(FW T7)

<400> SEQUENCE: 7
cccgcgaaat taatacgact cactatagg                                         29

<210> SEQ ID NO 8
<211> LENGTH: 55
<212> TYPE: DNA
<213> ORGANISM: Artificial sequence
<220> FEATURE:
<223> OTHER INFORMATION: Primer 2(RV-109-EcoRI-Rhf-2)

<400> SEQUENCE: 8
cggttgatgg cggtgcagca cgaattccat tttcacacgg aagctcttta atccg            55

<210> SEQ ID NO 9
<211> LENGTH: 55
<212> TYPE: DNA
<213> ORGANISM: Artificial sequence
<220> FEATURE:
<223> OTHER INFORMATION: Primer 3(FW Rhf-EcoRI-109-2)

<400> SEQUENCE: 9
cggattaaag agcttccgtg tgaaaatgga attcgtgctg caccgccatc aaccg             55

<210> SEQ ID NO 10
<211> LENGTH: 34
<212> TYPE: DNA
<213> ORGANISM: Artificial sequence
<220> FEATURE:
<223> OTHER INFORMATION: Primer 4(RV-Rhf-Link-Red-HindIII+EcoRV)

<400> SEQUENCE: 10
aagatatcaa gctttcagag tcgcagggcc agcc                                   34

<210> SEQ ID NO 11
<211> LENGTH: 33
<212> TYPE: DNA
<213> ORGANISM: Artificial sequence
<220> FEATURE:
<223> OTHER INFORMATION: Primer 5(PCR cyp109B1 A11)

<400> SEQUENCE: 11
cctgcaggtt acattttcac acggaagctc ttt                                    33
```